United States Patent

Bien et al.

[11] Patent Number: 5,885,268
[45] Date of Patent: Mar. 23, 1999

[54] ABSORBENT STRUCTURES HAVING DECOUPLED TOPSHEET AND TOPSHEET SUPPORT STRIP

[75] Inventors: Denise Jean Bien, Cincinnati; Cynthia Lee Alvis, Fairfield; Nicholas Albert Ahr, Cincinnati; Ronald Ray McFall, West Chester; Thomas Ward Osborn, III, Cincinnati, all of Ohio

[73] Assignee: The Procter & Gamble Company, Cincinnati, Ohio

[21] Appl. No.: 768,726

[22] Filed: Dec. 18, 1996

[51] Int. Cl.⁶ ...................................................... A61F 13/16
[52] U.S. Cl. ................... 604/385.1; 604/378; 604/385.2
[58] Field of Search ............... 604/385.1, 385.2, 604/386, 387, 378

[56] References Cited

U.S. PATENT DOCUMENTS

| | | | |
|---|---|---|---|
| H1614 | 11/1996 | Mayer et al. | 604/378 |
| 2,866,459 | 12/1958 | Sobelson. | |
| 3,371,668 | 3/1968 | Johnson. | |
| 4,425,129 | 1/1984 | Karami | 604/385.2 |
| 4,524,577 | 6/1985 | Ito et al.. | |
| 4,808,177 | 2/1989 | DesMarais et al. | 604/385.2 |
| 4,838,886 | 6/1989 | Kent | 604/392 |
| 4,847,134 | 7/1989 | Fahrenkrug et al. | 428/138 |
| 4,892,536 | 1/1990 | DesMarais et al. | 604/385.2 |
| 4,935,021 | 6/1990 | Huffman et al. | 604/385.2 |
| 5,007,906 | 4/1991 | Osborn, III et al. | 604/385.1 |
| 5,037,417 | 8/1991 | Ternstrom et al. | 609/385.2 |
| 5,264,268 | 11/1993 | Luceri et al. | 428/138 |
| 5,295,988 | 3/1994 | Muckenfuhs et al. | 604/385.2 |
| 5,324,278 | 6/1994 | Visscher et al. | 604/385.1 |
| 5,411,498 | 5/1995 | Fahrenkrug et al. | 604/385.2 |
| 5,431,991 | 7/1995 | Quantrille et al. | 428/109 |
| 5,451,219 | 9/1995 | Suzuki et al. | 604/385.2 |
| 5,460,623 | 10/1995 | Emenaker et al. | 604/368 |
| 5,520,674 | 5/1996 | Lavon et al. | 604/385.1 |
| 5,558,656 | 9/1996 | Bergman | 604/385.1 |
| 5,591,148 | 1/1997 | McFall et al. | 604/385.1 |
| 5,593,400 | 1/1997 | O'Leary | 604/385.2 |

FOREIGN PATENT DOCUMENTS

| | | |
|---|---|---|
| 2153024 | 6/1995 | Canada. |
| WO 93/01785 | 2/1993 | WIPO. |
| WO 94/02098 | 2/1994 | WIPO. |
| WO 95/20931 | 8/1995 | WIPO. |
| WO 95/32699 | 12/1995 | WIPO. |
| WO 96/12458 | 5/1996 | WIPO. |
| WO 96/14039 | 5/1996 | WIPO. |
| WO 96/23471 | 8/1996 | WIPO. |
| WO 97/07763 | 3/1997 | WIPO. |
| WO 97/39710 | 10/1997 | WIPO. |
| WO 97/45082 | 12/1997 | WIPO. |

*Primary Examiner*—Mark O. Polutta
*Attorney, Agent, or Firm*—Steven W. Miller; Jeffrey V. Bamber; Edward J. Milbrada

[57] ABSTRACT

Absorbent structures comprising a topsheet, a backsheet with an absorbent core between the topsheet and the backsheet are described. The absorbent structures further comprise a support strip that provides a contractive force that causes at least a portion of the support strip and at least a portion of the topsheet to become decoupled from the absorbent core. Alternative embodiments of the absorbent structure include laterally extending flaps and an abbreviated undergarment.

22 Claims, 12 Drawing Sheets

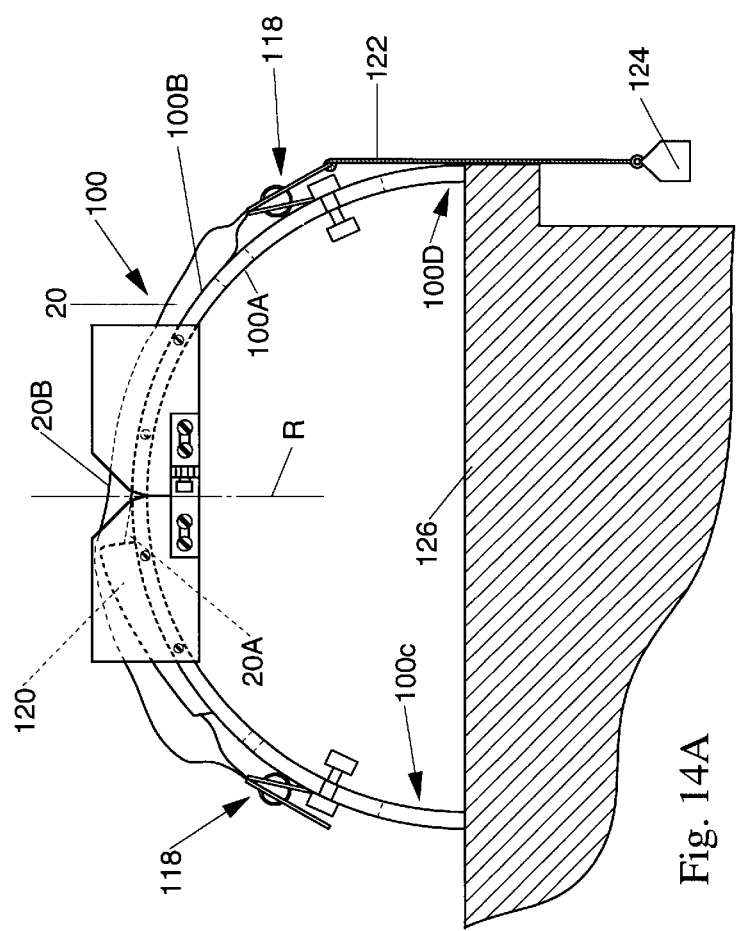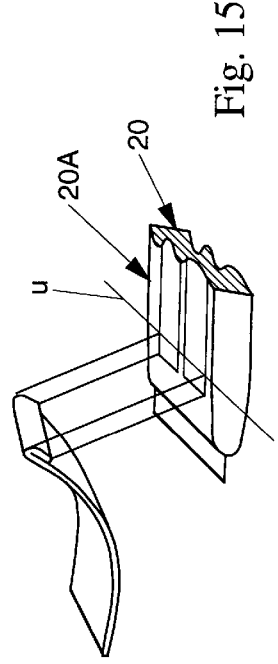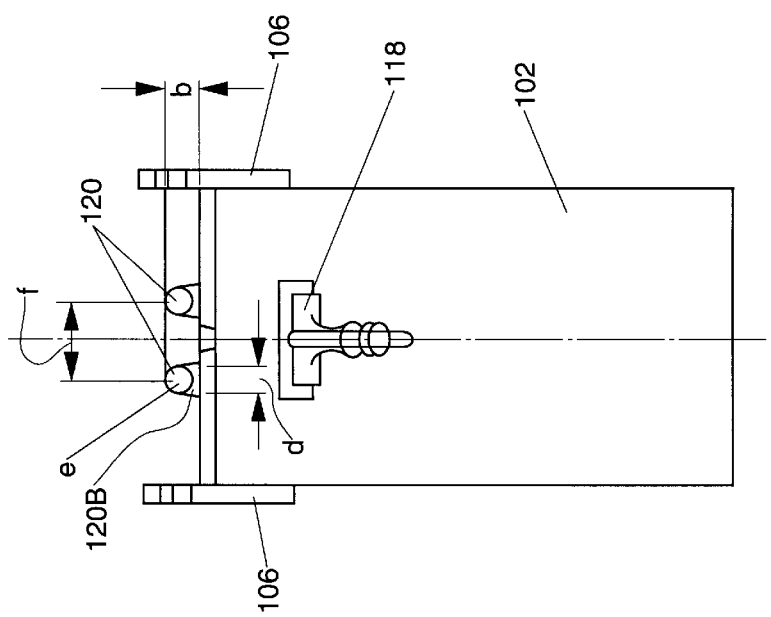

ABSORBENT STRUCTURES HAVING DECOUPLED TOPSHEET AND TOPSHEET SUPPORT STRIP

FIELD OF THE INVENTION

The present invention relates to an absorbent article suitable for use in absorbing bodily fluids. Specifically, the present invention relates to an absorbent article with a decoupled topsheet and a topsheet support strip which aid in reliably maintaining contact between the absorbent article and a female wearer's body.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling.

It is desirable to provide absorbent articles that reduce the risk of leakage of bodily fluids that can result in soiling of clothing or bedding. It is also desirable to provide such absorbent articles with excellent body fit such that the absorbent article conforms to a female wearer's anatomy. For example, it is particularly desirable that at least a portion of such an absorbent article fit comfortably within female wearer's interlabial crevice while, at the same time, fitting into the wearer's gluteal groove. It is further desirable that such absorbent articles maintain such conformity (i.e. reliable body contact) throughout the full range of wearer motions as a means for reducing such leakage. It is still further desirable that such absorbent articles be conveniently disposable.

One means the art has used to respond to such needs has been to provide stretchable absorbent articles. For example, providing stretchability to catamenial products has been contemplated by the art. U.S. Pat. No. 3,371,668, issued to Johnson on Mar. 5, 1968, is directed to a sanitary napkin employing a nonwoven fabric with a cover said to have machine direction elasticity. The described fabric comprises a nonwoven web of fibers having a plurality of elastic means, in extended condition, secured to the web. Upon their release, the fabric contracts in the length direction and is characterized by a plurality of substantially parallel buckled areas said to have improved bulk. While this improved bulk may provide an improvement in body contact over a catamenial product lacking such buckled areas, the buckles do not readily conform to a female wearer's anatomy. For example, it is unlikely that the Johnson device would conform, even partially, to a female wearer's interlabial crevice.

Another absorbent article that uses stretch to provide improved contact with a wearer's body is described in PCT Application No. WO 95/20931 published in the name of Osborn, et al. on Aug. 10, 1995. The absorbent articles described therein include sanitary napkins, pantiliners and the like. Such absorbent articles are described as comprising at least some extensible components. Preferably, the topsheet, the backsheet and the absorbent core are all extensible or are provided with extensible regions. While such absorbent articles provide improved contact with a wearers body, as exemplified by the Lift results described in the above mentioned PCT Application, there is a continuing need to provide even better body contact and body conformity throughout the entire range of wearer motions.

U.S. Pat. No. 5,411,498, issued to Fahrenkrug, et al. on May 2, 1995 describes an absorbent garment having a fluid pervious inner layer, an outer layer, an absorbent structure disposed between the inner and outer layers, and a plurality of elastomeric strands located between the inner and outer layers, at least one of the strands being positioned between the inner layer and the absorbent structure and at least one of the strands being positioned between the absorbent structure and the outer layer. In a relaxed state the strands are said to cause the absorbent structure to be gathered. Such gathers are said to allow the garment to expand longitudinally The positioning of the strands is also said to cause the absorbent garment to have a pocket configuration. One embodiment of the Fahrenkrug, et al. device is also provided with attachment means for fitting around the hips of a wearer. While such a structure may allow a catamenial pad to follow wearer movement better than a catamenial pad that is attached to an undergarment, the pocket configuration may not reliably contact a wearer's pudendal region with a resulting risk of leakage and staining.

Another means used by the art to provide more intimate contact between an absorbent article and a wearer's body is to allow various portions of the absorbent article to separate, while the absorbent article, as a whole, remains a unitary structure. For example, U.S. Pat. No. 5,007,906, issued to Osborn, III, et al. on Apr. 16, 1991 describes a sanitary napkin having a topsheet that is joined to an absorbent core. The topsheet and the associated core are decoupled from the backsheet so that the topsheet and the backsheet can separate in the "z" direction. The topsheet and the backsheet are joined at one transverse end to form a hinge. The opposite end is free to rise. An interliner joined to the absorbent core may be provided. The interliner constrains flow of bodily discharges toward the backsheet While such structure allows the topsheet and the core to be decoupled from the backsheet with a resulting improvement in response to wearer movement, improvements are needed to provide better conformity to the various shapes of portions of a wearer's pudendal region.

Similarly, PCT Application WO 94/02098, published in the name of Osborn, III, et al. on Feb. 3, 1994, describes a menstrual short with a catamenial pad assembly connectable thereto. The catamenial pad assembly comprises an absorbent member and a cinch member. The cinch member biases (lifts) the absorbent member into a wearer's gluteal groove and against her perineum. While this system of menstrual short and catamenial pad assembly provides improved body contact and wearer comfort when compared to other menstrual undergarments, such as Japanese menstrual shorts, the entire catamenial pad is lifted and, as a result, the pad may not fully conform to a wearer's body.

The sanitary napkin described in U.S. Pat. No. 5,324,278, issued to Visscher on Jun. 28, 1994 also describes a liquid pervious spacing structure positioned between the absorbent core and the topsheet thereof The spacing structure responds to lateral compressive forces from a wearer's thighs by moving the topsheet upward and away from the absorbent core. While such a sanitary napkin provides improved body contact, it depends on lateral compressive forces from a wearer's legs to move the topsheet upward. When such compressive forces are reduced or absent, such as when a wearer's legs are spread, the separation between the topsheet and the absorbent core is reduced, possibly reducing body contact.

Yet another device where portions of the absorbent article separate is described in PCT Application WO 96/12458, published on May 2, 1996 in the names of Endres, et al. The device described therein is a diaper comprising a garment shell and a liquid control member. The garment shell comprises a backsheet layer, an absorbent assembly disposed on the backsheet layer and a liquid permeable bodyside layer bonded to the backsheet layer about the periphery of the garment shell so the absorbent assembly is sandwiched between the bodyside layer and the backsheet layer. The liquid control member has two opposing stationary zones with an elasticized zone therebetween. The liquid control member is disposed on the bodyside layer and joined thereto at each stationary zone with the elasticized zone being unattached. The illustrated liquid control member comprises a liquid permeable material, spaced apart lateral barriers, and elastic members joined to the lateral barriers. An alternative embodiment (not shown) can comprise a single elastic member that is desirably formed of a liquid permeable material. While such structures may provide improved body contact, they would fail to provide the conformity to a female wearer's anatomy that can result in reduced leakage.

While all of the above mentioned devices, in some degree, are aimed at improving body contact, there is still a need for improvements in body fit and responsiveness to wearer motion. Thus, it is an object of the present invention to provide an absorbent structure with improved contact with a female wearer's pudendal region. Specifically, it is an object of the present invention to provide comfortable interlabial fit while, at the same time, providing comfortable gluteal groove fit. It is a further object of the present invention to provide an absorbent structure that can reliably maintain body contact throughout a full range of wearer motions. It is still a further object of the present invention to provide an absorbent article which can be worn in place of a wearer's undergarments and can be readily disposed of when the absorbent capacity of the article is reached; eliminating the need to treat soiled undergarments.

SUMMARY OF THE INVENTION

The present invention is an absorbent article suitable for use as a catamenial device or as a urinary incontinence device for a female wearer. Components of the absorbent article of the present invention decouple from each other which results in better conformity to a wearer's pudendal region throughout the full range of wearer motions.

A preferred embodiment of the present invention comprises a liquid impervious backsheet, an absorbent core disposed on the backsheet and a liquid pervious topsheet disposed on the absorbent core. The absorbent article of the present invention further comprises an elastically extensible support strip which contracts and lifts the topsheet in the vertical direction so they become decoupled from the backsheet and the remaining portion of the core. This decoupling results in improved contact of the absorbent article with a wearer's pudendal region. In a preferred embodiment this support strip comprises a laminate of an elastic member and a nonwoven material.

Preferred embodiments of the present invention further comprise longitudinally extending cuffs and means for attaching the absorbent article to a wearer's undergarments.

Alternative embodiments of the present invention include:

Decoupling a portion of the absorbent core so it is also lifted by the support strip in the vertical direction.

Providing the absorbent article with laterally extending flaps.

An abbreviated panty having an elastically extensible shell portion that holds an absorbent portion of the abbreviated panty in close body contact. The absorbent portion has substantially the same structure as is described above. The elastically extensible shell portion preferably comprises a laminate comprising an elastic member that is disposed between two plies of a nonwoven material.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 14 is a cross-sectional view of one of the PLEXIGLAS plates used in the Lift Test apparatus as taken along line 13—13 of FIG. 12.

FIG. 14A is a side view of the calibration of the Lift Test apparatus for a particular absorbent article.

FIG. 15 is a perspective view of the manner in which the tape pieces are attached to the end of an absorbent article (shown partially cut away) in preparation for the Lift Test.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the absorbent structure 20, shown in FIG. 1. Such absorbent structures have utility as catamenial devices (e.g. sanitary napkins) and urinary incontinence devices for female wearers. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). As used herein, the term "pudendal" refers to the externally visible female genitalia. As used herein, the term "urinary incontinence device" refers to those absorbent articles intended to absorb bodily exudates, such as urine and other liquids from female wearers while allowing the anus to remain unobstructed.

General Description of the Absorbent Structure

Figure 1:
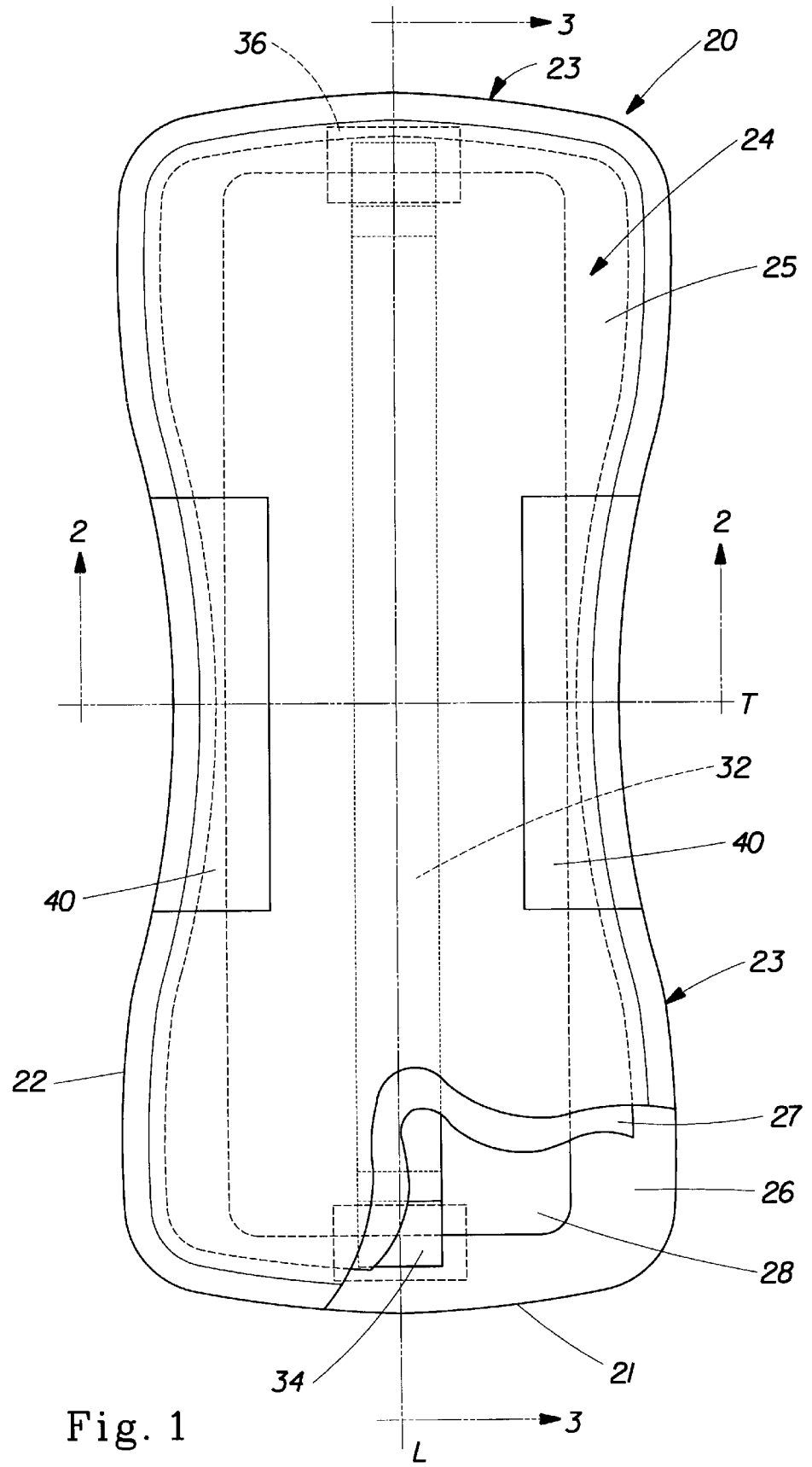
FIG. 1 is a top plan view of a preferred embodiment of the absorbent article of the present invention in flat out state with portions of the structure being cut-away to more clearly show the construction thereof.

FIG. 1 is a plan view of the absorbent structure 20 of the present invention in its flat-out state with portions of the structure being cut-away to more clearly show the construction of the absorbent structure 20. As shown in FIG. 1, the absorbent structure 20 preferably comprises a liquid pervious topsheet 24, a liquid impervious backsheet 26 joined with the topsheet 24, an absorbent core 28 positioned between the topsheet 24 and the backsheet 26, and support strip 32 which is disposed between the topsheet 24 and the absorbent core 28.

The absorbent structure 20 has two surfaces, a liquid pervious body-contacting surface or "body surface" 20A and a liquid impervious garment surface 20B. The absorbent structure 20 is shown in FIG. 1 as viewed from its body surface 20A. The body surface 20A is intended to be worn adjacent to the body of the wearer. The garment surface 20B of the absorbent structure 20 (shown in FIG. 2) is on the opposite side and is intended to be placed adjacent to the wearer's undergarments when the absorbent structure 20 is worn. The body and garment surfaces of other elements of the present invention will be described in a similar manner with an "A" being appended to the reference number of the element to designate the body surface thereof and a "B" being appended to designate the garment surface thereof The absorbent structure 20 has two centerlines, a longitudinal centerline L and a transverse centerline T. The term "longitudinal", as used herein, refers to a line, axis or direction in the plane of the absorbent structure 20 that is generally aligned with (e.g., approximately parallel to) a vertical plane which bisects a standing wearer into left and right body halves when the absorbent structure 20 is worn. The terms "transverse" or "lateral" as used herein, are interchangeable, and refer to a line, axis or direction which lies within the plane of the absorbent structure 20 that is generally perpendicular to the longitudinal direction. FIG. 1 also shows that the absorbent structure 20 has a periphery 23 which is defined by the outer edges of the absorbent structure 20 in which the longitudinal edges are designated 22 and the end edges are designated 21.

As can also be seen in FIG. 1, the preferred embodiment of the absorbent structure 20 also comprises a pair of longitudinally extending cuffs 40. The cuffs 40 are disposed on the topsheet 24 adjacent each of the longitudinal edges 22 and are joined thereto.

Figure 2:
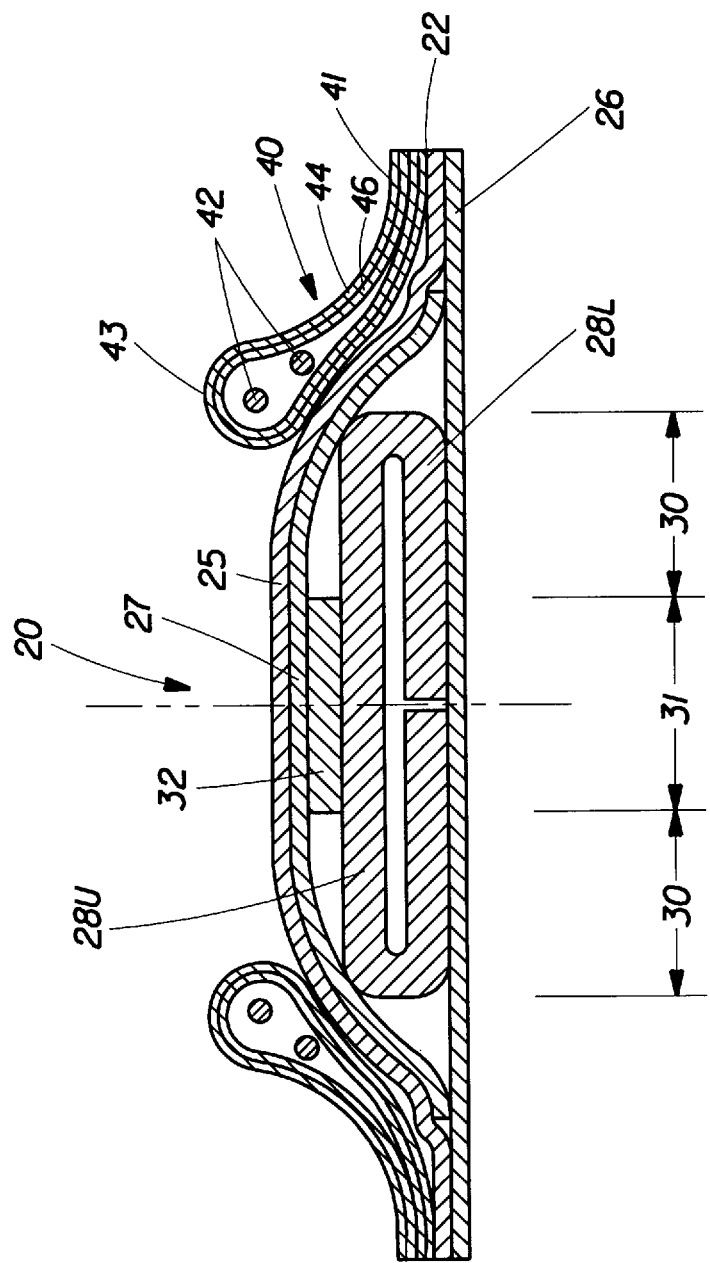
FIG. 2 is a transverse cross sectional view taken along line 2—2 of the absorbent article shown in FIG. 1.
Figure 3:
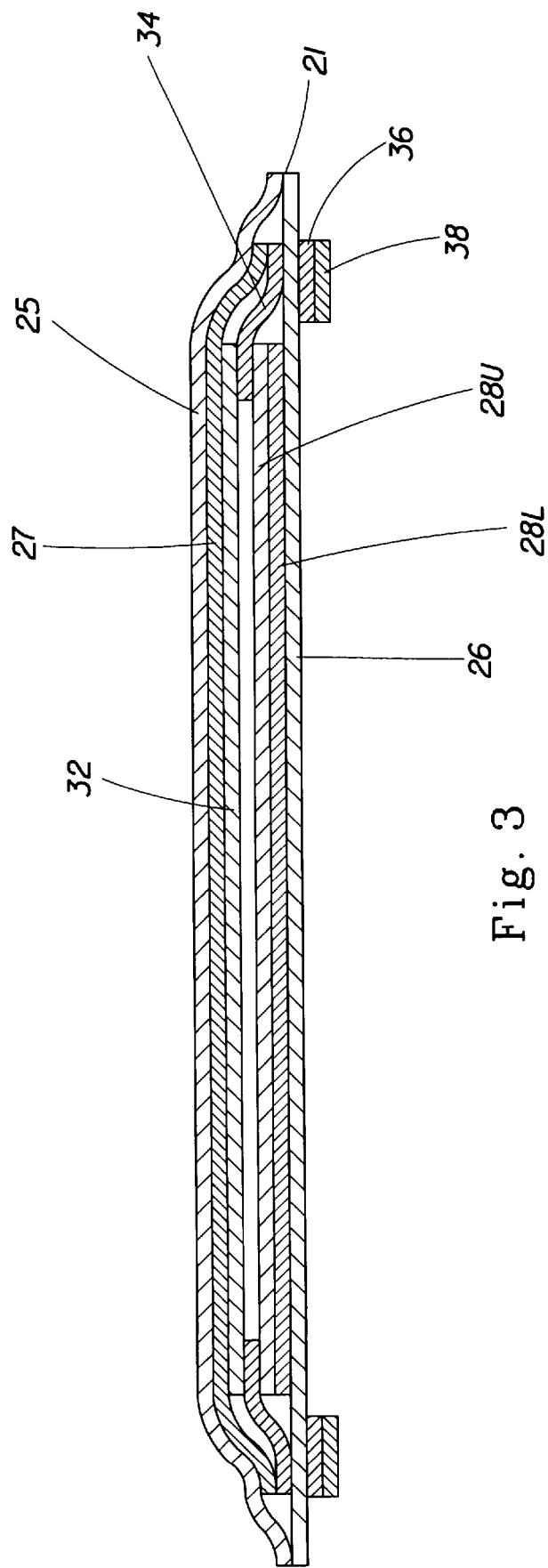
FIG. 3 is a longitudinal cross sectional view taken along line 3—3 of the absorbent article shown in FIG. 1.

FIG. 2 is a cross-sectional view of the absorbent structure 20 taken along section line 2—2 of FIG. 1. Similarly, FIG. 3 is a cross-sectional view of the absorbent structure 20 taken along section line 3—3 of FIG. 1. As can be seen most clearly in FIGS. 2 and 3, the preferred absorbent structure 20 also comprises a support strip 32 that is disposed between the absorbent core 28 and the topsheet 24. The support strip 32 lifts the topsheet 24 vertically separating it from the core 28. Such separation provides the absorbent structure 20 with improved body contact. As can also be seen in FIG. 2, the cuffs 40 comprise an elastic member 42 which lifts the cuffs 40 up and away from the plane of the topsheet 24, a body contacting member 44, and a barrier member 46.

While the topsheet, the backsheet, and the absorbent core may be assembled in a variety of well known configurations (including so called "tube" products or side flap products), preferred sanitary napkin configurations are described generally in U.S. Pat. No. 4,950,264, issued to Osborn on Aug. 21, 1990; U.S. Pat. No. 4,425,130, issued to DesMarais on Jan. 10, 1984; U.S. Pat. No. 4,321,924, issued to Ahr on Mar. 30, 1982; U.S. Pat. No. 4,589,876, issued to Van Tilburg on Aug. 18, 1987. The disclosure of each of these patents are hereby incorporated herein by reference. FIG. 1 shows a preferred embodiment of the absorbent structure 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 23. The topsheet 24 and the backsheet 26 are preferably joined to each other around this periphery 23. As is shown most clearly in FIG. 3, the support strip 32 is joined to the topsheet 24 along substantially its entire longitudinal length and to the absorbent core 28 at attachment sites 34.

The Absorbent Core

The absorbent core 28 may be any absorbent means which is capable of absorbing or retaining liquids (e.g., menses and/or urine). As shown in FIG. 1, the absorbent core 28 has a body surface, a garment surface, side edges, and end edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding, meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core 28 of the present invention are described in U.S. Pat. No. 4,950,264 which issued to Osborn on Aug. 21, 1990, U.S. Pat. No. 4,610,678 which issued to Weisman et al. on Sep. 9, 1986; U.S. Pat. No. 4,834,735 which issued to Alemany et al. on May 30, 1989; and European Patent Application No. 0 198 683, The Procter & Gamble Company, published Oct. 22, 1986 in the name of Duenk, et al. The disclosure of each of these patents is incorporated herein by reference.

A preferred embodiment of the absorbent core 28 comprises a blend of comminuted wood pulp and a superabsorbent polymer. A particularly preferred embodiment for the core 28 of the present invention has three longitudinally oriented trisections (a central trisection 31 flanked by two outboard trisections 30). The core 28 comprises a single layer of tissue or other suitable absorbent materials that is folded back on itself to create a dual ply structure 28U, 28L (shown in FIG. 2). The absorbent core 28 also preferably has superabsorbent polymer disposed between the two plies comprising the outboard trisections 30. Similar core structures are described in greater detail in commonly assigned U.S. Pat. No. 5,460,623, issued to Emenaker, et al. on Oct. 24, 1995, the disclosure of which is incorporated herein by reference.

The absorbent core is preferably made of an airlaid tissue. An airlaid tissue is preferred over a wet laid tissue because of its greater wet strength which avoids wet collapse and intrinsically higher void volume. The tissue should have properties which make it suitable for use in the absorbent structure 20 of the present invention. In particular, a tissue having a wet tensile strength of at least 100 grams per centimeter as determined by ASTM Standard Method D829-49 is preferred, so that the tissue recovers from lateral compression after being wetted by bodily fluids such as urine or menses. A suitable tissue is available from the Fort Howard Corporation of Green Bay, Wis. as grade 817.

The backsheet 26 and the topsheet 24 are positioned adjacent the garment surface 28B and the body surface 28A, respectively, of the absorbent core 28. As is shown in FIG. 3, the backsheet 26 is joined to the lower ply 28L of the absorbent core 28 by attachment means (not shown) such as those well known in the art. For example, the backsheet 26 may be secured to the lower ply 28L by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, the disclosure of which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. The disclosure of each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

In the preferred embodiment of the absorbent structure 20 shown in FIGS. 1–3, the topsheet 24 and the backsheet 26 are joined to each other about the periphery 23 using means similar to those discussed above. Further, the topsheet 24 is decoupled from the absorbent core 28. As used herein, the term "decoupled" refers to the independence of movement of two or more components of the absorbent structure 20 and requires separability of the components. As will be discussed in detail below with respect to the support strip 32, such decoupling enables the absorbent structure 20 of the present invention better conform to a wearer's body.

The Backsheet

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the absorbent structure 20 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 26 may permit vapors to escape from the absorbent core 28 (i.e., breathable) while still preventing exudates from passing through the backsheet 26.

The Topsheet

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fiber such as polyester, polypropylene, or polyethylene fibers) or from a combination of natural and synthetic fibers. In the preferred embodiment of the present invention shown in FIGS. 1–3, the topsheet 24 comprises a primary topsheet layer 25 and a secondary topsheet layer 27 which are described in detail below.

Primary Topsheet Layer

While any of the materials discussed above with respect to the topsheet 24 are suitable for use as the primary topsheet layer 25, a preferred primary topsheet layer topsheet comprises a nonwoven material. Nonwoven materials are preferred for use as the primary topsheet layer 25 because their soft tactile feel is comfortable for wearers. Suitable nonwoven materials include carded, air-laid, melt blown, or spun bonded materials. A preferred nonwoven material for use as the primary topsheet layer 25 may comprise carded, melt blown, or spun bonded nonwovens wherein the nonwoven material comprises either natural or synthetic fibers. A particularly preferred nonwoven material for the primary topsheet layer 25 comprises a hydrophilic, spun bonded material having a basis weight of about 0.68 ounces per square yard (23 grams per square meter) such as is supplied by Corovin GmbH of Penne, Germany as Corolind H23GSM.

Alternatively, the primary topsheet layer 25 may comprise an apertured formed film. Apertured formed films are suitable for use as the primary topsheet layer 25 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, which issued to Thompson on Dec. 30, 1975; U.S. Pat. No. 4,324,246, which issued to Mullane, et al. on Apr. 13, 1982; U.S. Pat. No. 4,342,314, which issued to Radel. et al. on Aug. 3, 1982; U.S. Pat. No. 4,463,045, which issued to Ahr et al. on Jul. 31, 1984; and U.S. Pat. No. 5,006,394, which issued to Baird on Apr. 9, 1991. The disclosure of each of these patents are incorporated herein by reference. A suitable primary topsheet layer 25 for the present invention is the formed film described in one or more of the above patents and marketed on sanitary napkins by The Procter & Gamble Company of Cincinnati, Ohio as "DRI-WEAVE".

In a preferred embodiment of the present invention, the body surface 25A of the primary topsheet layer 25 is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the primary topsheet layer 25 such as is described in U.S. patent application Ser. No. 07/794,745, filed on Nov. 19, 1991 by Aziz, et al., the disclosure of which is incorporated herein by reference. Alternatively, the body surface of the primary topsheet layer 25 can be made hydrophilic by treating it with a surfactant such as is described in the above referenced U.S. Pat. No. 4,950,254.

Secondary Topsheet Layer

In the preferred embodiment of the present invention shown in FIGS. 1–4, a secondary topsheet layer 27 is positioned between the primary topsheet layer 25 and the absorbent core 28. The secondary topsheet layer 27 may serve several functions including improving wicking of exudates over and into the absorbent core 28. There are several reasons why the improved wicking of exudates is important, including providing a more even distribution of the exudates throughout the absorbent core and allowing the absorbent structure 20 to be made relatively thin. (The wicking referred to herein may encompass the transportation of liquids in one, two or all directions (i.e., in the x-y plane and/or in the z-direction). The secondary topsheet layer 27 may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of absorbent articles having a secondary topsheet layer are more fully described in the above-referenced U.S. Pat. No. 4,950,264 and in U.S. patent application Ser. No. 07/810,774, filed Dec. 17, 1991 in the names of Cree, et al and published as PCT Application Serial No. WO 93/11725 on Jun. 24, 1993. The disclosure of each of these publications is incorporated herein by reference.

Preferably, the secondary topsheet layer 27 is formed from a natural or synthetic nonwoven fabric. Suitable materials for use as a secondary topsheet 27 include an air laid tissue having a basis weight of about 35 grams per square meter (gsm) which is available from Merfin Hygiene Products Ltd., Delta, BC, Canada; a nonwoven fabric of spunbonded polypropylene fibers available from the Fiberweb Corporation of Simpsonville, S.C. under the tradename CELESTRA; and a nonwoven fabric formed of bicomponent fibers which have a polyethylene sheath and a polyurethane core, which is available from the Havix Company, of Japan, as S2416. A particularly preferred material for use as a secondary topsheet 27 is the air laid tissue having a basis weight between about 30 pounds per 3000 square feet (49 g/square mater) and about 45 pounds per 3000 square feet (74 g/square meter), preferably about 35 pounds per 3000 square feet (57 g/square meter) which is available from Fort Howard Corporation of Green Bay Wis.

In a preferred embodiment, the secondary topsheet layer 27 may be joined to the primary topsheet layer 25 by any of the conventional means for joining webs together. Most preferably, the means for joining the primary topsheet layer 25 to the secondary topsheet layer 27 comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. The disclosure of each of these patents is incorporated herein by reference.

In an alternative embodiment of the present invention, the secondary topsheet layer 27 may be treated to "draw" fluids therethrough. A suitable treatment for such purpose is flocking. Flocking is described in general terms in the pamphlet: *Design with Flock in Mind*™, published by the American Flock Association of Boston, Mass. The American Flock Association also publishes a list of companies that provide flocking services. Suitable flocking fibers include both natural fibers, such as wood pulp fibers (e.g. northern sulfite kraft or eucalyptus) or cotton fibers, and synthetic fibers, such as polyethylene fibers, polypropylene fibers, polyester fibers, nylon fibers and the like. Preferably, the flocking fibers are either inherently hydrophilic or treated to be hydrophilic. Suitable flocking adhesives are substantially the same as those discussed herein as being suitable for joining the absorbent core 28 to the backsheet 26.

Without being bound by theory, the Applicants believe flocking or a similar treatment draws fluids through the primary topsheet layer 25 and the secondary topsheet layer 27 by disrupting the meniscus of any fluid that may bridge any capillary channels that are present in the primary and secondary topsheet layers 25, 27. Once the fluid has been drawn through the secondary topsheet layer 27 to the garment surface 27B thereof, it has been found to drip therefrom onto the body surface 28A of the absorbent core 28 for absorption.

Cuffs

With further reference to FIGS. 1 and 2, the preferred embodiment of the absorbent structure 20 of the present invention further comprises a pair of cuffs 40. Because the distal edge 43 of a cuff 40 is lifted up and away from the body surface 24A of the topsheet 24, the cuffs 40 act as barriers to lateral flow of such bodily fluids as may be disposed on the topsheet 24 helping to prevent leakage with resulting staining of garments or bedding.

As can be seen in FIG. 2, a cuff 40 is disposed on the body surface 24A of the topsheet 24 adjacent each longitudinal edge 22. The cuffs 40 are disposed in an elongated state, and are joined to the topsheet 24 in that elongated state as is described below. As will be easily understood by reference to FIG. 2, each of the cuffs 40 comprises at least an elastic member 42 and a body contacting member 44. Preferably, as is shown in FIG. 2, each cuff 40 comprises an elastic member 42, a body contacting member 44 and a barrier member 46. The cuffs 40 are disposed on the topsheet 24 along at least a portion of each longitudinal edge 22. For example, the cuffs 40 could be disposed along substantially the entire length of each longitudinal edge 22. Preferably, however, the cuffs 40 are disposed symmetrically about the transverse centerline T along a portion of each longitudinal edge 22. Preferably, the fully extended length of each cuff 40 is between about 15% and about 87% of the fully extended length of the longitudinal edge 22. More preferably, the fully extended length of each cuff 40 is between about 15% and about 75% of the fully extended length of the longitudinal edge 22. In a particularly preferred embodiment of the absorbent structure 20, the fully extended length of the cuff 40 is about 30% of the fully extended length of the longitudinal edge 22. As used herein the "fully extended length" of an element is the length measured when the absorbent structure 20 is in a fully flat out position with all elastic contractions pulled out.

As can be seen in FIG. 2, each cuff 40 is formed by disposing the barrier member 46 on the body contacting member 44 and joining them using means known to the art to form a laminate. The elastic member 42 is then elongated prior to joining it to the laminate described above. The elastic member 42 may be elongated to any length suitable to gather or contract the cuffs 40 without generating excessive forces that could adversely affect the skin of the wearer or the shape of the absorbent structure 20. It is preferred that the elongation may be relatively small. Generally, the elastic member 42 may be elongated from about 5% to about 100%, more preferably from about 50% to about 90%. In a preferred embodiment, the elastic member is elongated about 60% (160% of its original length) and joined to the laminate. The laminate is then folded about the elongated elastic member 42 in a c-fold to form proximal edge 41 and distal edge 43 of cuff 40. While still in an elongated state, each cuff 40 is disposed on body surface 24A of topsheet 24 adjacent a longitudinal edge 22 thereof and joined thereto using means known to the art such that proximal edge 41 of cuff 40 and longitudinal edge 22 are juxtaposed.

Preferably the body contacting member 44 has properties similar to the properties of the topsheet 24 and the barrier member 46 has properties similar to the backsheet 26. As a result, materials suitable for use as a topsheet 24 are also suitable for use as a body contacting member 44 and materials suitable for use as a backsheet 26 are also suitable for use as a barrier member 46. Any elastically extensible materials known to the art are suitable for use as the elastic member 42. For example, elastically extensible film materials and laminates thereof with nonwoven materials; heat shrinkable elastically extensible materials and laminates thereof with nonwoven materials; elastically extensible strand materials and laminates thereof with nonwoven materials; and elastically extensible scrim materials are all suitable for use as an elastic member 42.

One skilled in the art will recognize that a single material may function as more than one of the members described above. A particularly preferred material for the cuff 40 of the present invention is the bilaminate of an elastically extensible film material and a nonwoven material which is described in commonly assigned U.S. Pat. No. 5,234,422, issued to Sneller, et al. on Aug. 10, 1993, the disclosure of which is incorporated herein by reference.

Panty Attachment Means

In use, the absorbent structure 20 can be held in place by any support means as are well-known for such purposes. While the panty attachment means 36 can take any suitable configuration as may be known to the art, preferably, as can be seen in FIG. 3, panty attachment means 36 comprises two portions, a portion being disposed on the garment surface 26B of the backsheet adjacent each end edge 21 of the absorbent structure 20. Such placement allows that part of the absorbent structure 20 that lies between the two portions of the attachment means 36 to rise above the plane of the crotch region of a wearer's undergarment in response to wearer movement in order that the absorbent structure 20 continue to maintain contact with the wearer's body.

The panty attachment means can comprise any material known to the art as suitable for such purpose. In particular, the panty attachment means 36 can comprise mechanical attachment means or adhesive attachment means as are known to the art. Preferably, the panty attachment means 36 comprises an adhesive material. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697, the disclosure of which is incorporated by reference.

Preferably, the absorbent structure is placed in the user's undergarment or panty and secured to the crotch area thereof by a fastener such as an adhesive. The adhesive provides a means for securing the sanitary napkin in the crotch portion of the panty. Thus, a portion or all of the garment surface 26B of the backsheet 26 is coated with adhesive. Before the sanitary napkin is placed in use, the pressure-sensitive adhesive is typically covered with a removable release liner 38 in order to keep the adhesive from drying out or adhering to a surface other than the crotch portion of the panty prior to use. Suitable release liners are also described in the above-referenced U.S. Pat. No. 4,917,697. Any commercially available materials commonly used for such purposes can be utilized herein. Non-limiting examples of suitable materials for the release liner 38 are BL30MG-A Silox E1/0 and BL30MGA Silox 4P/O both of which are manufactured by the Akrosil Corporation of Menasha, Wis.

The absorbent structure 20 of the present invention is used by removing the release liner and thereafter placing the structure in the crotch area of a panty so that the adhesive contacts the panty. The panty is then pulled on in the conventional manner. The adhesive maintains the absorbent structure in its position within the panty during use.

Support Strip

The support strip 32 is particularly suited for providing the absorbent structure 20 with the ability to fit in close contact with and conform to the contours of the wearer's body, and to acquire and absorb bodily exudates from the wearer's body immediately upon discharge therefrom. The support strip 32 provides a contractive force that lifts the topsheet 24 (i.e. primary topsheet layer 25 and the secondary topsheet layer 27) vertically up and away from the absorbent core 28 such that they closely contact a wearer's pudendal region. That is, the topsheet 24 is decoupled from the absorbent core 28, allowing the support strip 32 to lift the topsheet 24 into contact with a wearer's pudendal region. Because the topsheet 24 is soft and conforming, this lifting action enables the absorbent structure 20 to accommodate to the shape of a wearer's body. In particular, the absorbent structure 20 is both able to conform to fit comfortably in the space between the wearer's labia, and to occupy the relatively large area in the wearer's gluteal groove. As a result, the absorbent structure 20 is able to stay in close proximity to a wearer's vaginal introitus (if the absorbent structure 20 is a catamenial device) or the wearer's urethra (if the absorbent structure is a urinary incontinence device) and to be in position to receive any discharges of bodily fluids therefrom.

The absorbent structure 20 of the present invention, as discussed above, preferably conforms closely to the wearer's body during use, and has a large area that is in actual contact with the wearer's body during use. The Lift Test is a laboratory method for approximating the potential of an absorbent article to achieve good body contact. The procedure for measuring Lift is set forth in general terms in the TEST METHODS section below and in detail in U.S. patent application Ser. No. 08/192,240, filed on Feb. 4, 1994 in the names of Osborn, et al. and published as PCT application No. WO 95/20931 on Aug. 10, 1995 the disclosure of which is incorporated herein by reference. The Lift can be measured at several different points in the Lift Test apparatus. These points can be thought of as representing a wearer's introitus, perineum, and the crevice between the wearer's buttocks (or "gluteal groove"). It should be understood, however, that the points on the test apparatus are intended to provide a consistent basis for comparing the Lift of different absorbent articles. The test apparatus and the points thereon are by no means intended to conform identically to a female wearer's anatomy. Table 1 compares the Lift at the corresponding first, second, and third positions in the Lift Test apparatus, respectively, of various embodiments of an absorbent structure according to the present invention where the support strip 32 has been prestretched to varying degrees before attaching it to the topsheet 24 and the absorbent core 28 (see discussion below) with Lift data on a prior art absorbent product that uses stretch for improved body fit and Lift data on a commercially available absorbent product.

TABLE 1

| Product | Lift in Millimeters at Position | | |
| --- | --- | --- | --- |
| | 1 | 2 | 3 |
| Prototype of Present Invention | | | |
| 9% Prestretch | 8 | 5 | 5 |
| 38% Prestretch | 26 | 19 | 13 |
| 100% Prestretch | 23 | 17 | 18 |
| Absorbent article of WO 95/20931* | 10 | 8 | 12 |
| Always ® Long Ultra with Wings* | 3 | 0 | 2.5 |

*Data from WO 95/20931

As can be seen, when the support strip 32 has been prestretched by about 38%, Lift in the first and second positions is substantially improved (more than doubled) when compared to absorbent articles of the prior art without substantial degradation in the third position. The absorbent structure 20 of the present invention preferably has a Lift at the first position in the Lift Test apparatus of greater than about 19 mm, a Lift at the second position of greater than about 12 mm, and a Lift at the third position of greater than about 8 mm.

As noted above, the support strip 32 is positioned between the topsheet 24 and the absorbent core 28. At least some portion of body surface 32A of the support strip 32 contacts the topsheet. This area of contact, determined by the length and width of the support strip 32, can affect the performance of the absorbent structure 20.

To insure that the support strip 32 does not unacceptably interfere with absorption of bodily fluids if an impervious material is used for the support strip 32, the support strip can occupy only a portion of the lateral width of the absorbent structure 20. Also, if the support strip 32 is too narrow, it can cause wearer discomfort by "cutting" into her body. It has been found that support strips 32 having between about 16% and 50% of the lateral width of the absorbent structure 20, when measured at the transverse centerline T thereof, provide a suitable balance of absorption, lift and wearer comfort. Preferably the lateral width of the support strip 32 is about 33% of the lateral width of the absorbent structure 20. For a preferred embodiment of the present invention having a lateral width of about 3 inches (7.6 cm), a support strip 32 having a width between about 0.5 inch (1.2 cm) and 1.5 inch (3.8 cm) is suitable. Preferably the width of such a preferred support strip 32 is about 1 inch (2.5 cm).

The longitudinal positioning of the support strip 32 is similarly important. In particular, as is shown most clearly in FIG. 3, the fully extended distance D along the longitudinal centerline L between the transverse centerline T and attachment site 34 where the support strip 32 is joined to the absorbent core 28 is important. In particular, if the distance D is too short, there will be insufficient Lift to insure that the topsheet conforms to both the space between the labia and to the gluteal groove and, if D is too long for an impermeable support strip 32, such an impermeable support strip 32 could interfere with absorption. Preferably, the support strip 32 is longitudinally centered about the transverse centerline T and the fully extended distance D is greater than about 75% of the length of the absorbent core 28 and less than the length of the absorbent structure 20 when the absorbent structure 20 is fully extended. More preferably, the support strip 32 is substantially the same length as the absorbent core 28 when the absorbent structure 20 is fully extended (i.e. D is about 100% of the length of the absorbent core 28).

In order that the support strip 32 may lift the topsheet 24, the support strip 32 is preferably joined to the topsheet 24 along substantially its entire longitudinal length. The support strip is joined to the absorbent core 28 only adjacent each end edge 21 of the absorbent structure 20 at attachment sites 34. As used herein, the term "joined" encompasses configurations whereby an element is directly secured to another element by affixing the element directly to the other element, and configurations whereby the element is indirectly secured to the other element by affixing the element to an intermediate member(s) which in turn is affixed to the other element. The support strip 32 and the topsheet 24 are joined using means familiar to those skilled in the art such as adhesive bonding, ultrasonic welding, or thermal bonding which is carried out in a multiplicity of discrete areas. A preferred means for joining the support strip 32 and the topsheet 24 comprises adhesive filaments swirled into a spiral pattern as discussed with respect to joining the primary topsheet layer 25 to the secondary topsheet layer 27 above. The support strip 32 and the absorbent core 28 are joined at attachment sites 34 using means known those skilled in the art as are discussed above with respect to joining the support strip 32 and the topsheet 24. Preferably, the support strip 32 is joined to the absorbent core 28 using adhesive means.

As noted above for the preferred embodiment of the present invention, the support strip 32 is prestretched before it is joined to the topsheet 24 and the absorbent core 28. As used herein, a "prestretched" material is one where the material has been stretched to a length greater than its relaxed length before being further acted on by additional processing steps. Referring again to Table 1, the support strip 32 is preferably prestretched by at least about 30% (i.e.

the support strip 32 is stretched to about 130% of its unstretched length). Without being bound by theory, the applicants believe the Lift benefit shown in Table 1 when comparing the absorbent structure of the present invention where the support strip 32 has been prestretched by more than 30% to the absorbent article of PCT Application WO 95/20931 can be attributed to the fact that the topsheet 24 is decoupled from the absorbent core 28 and, therefore, can more readily conform to the slit 114 of the Lift Test apparatus (FIG. 10.

The support strip 32 preferably comprises an elastic member. More preferably, the support strip 32 comprises a resilient material which has a low stretch modulus. Such low stretch modulus helps insure that the contractive force provided by the support strip 32 will not cause wearer discomfort. As used herein a resilient material is a material which can be elongated by at least about 25 percent of its relaxed length and which will recover, upon release of the applied force, at least about 10 percent of its elongation. It is generally preferred that a resilient material of the present invention be capable of being elongated by at least about 30 percent, more preferably by at least about 50 percent, of its relaxed length and recover, upon release of an applied force, at least about 75 percent of its elongation, preferably at least about 85 percent. Suitable materials for use with the present invention will have a stretch modulus of between about 50 (g/cm)/% and about 100 (g/cm)/% when measured according to the method described in the TEST METHODS section below. Preferably, the stretch modulus is between about 80 (g/cm)/% and about 90 (g/cm)/%.

Materials suitable for use as the support strip 32 include: elastically extensible film materials and laminates thereof with nonwoven materials; heat shrinkable elastically extensible materials and laminates thereof with nonwoven materials; elastically extensible strand materials and laminates thereof with nonwoven materials; and elastically extensible scrim materials. Alternatively, the support strip 32 can comprise materials such as those which:

1) foreshorten and become elastic following a specific treatment such as heating including those described in U.S. Pat. No. 4,515,595, issued to Kievit, et al. on May 7, 1985, in U.S. Pat. No. 3,819,401, issued to Massengale et al. on Jun. 25, 1974, and in U.S. Pat. No. 3,912,565, issued to Koch et al. on Oct. 14, 1975, or structures incorporating such foreshortening materials; or 2) foreshorten upon exposure to water or aqueous solutions, such as the twisted yarns described in U.S. Pat. No. 4,524,577, issued to Ito, et al. on Jun. 25, 1985 or structures incorporating such foreshortening materials.

(the disclosure of each of these patents is incorporated herein by reference). A suitable material for use as a support strip 32 is a laminate of an elastically extensive film material which is available as EXX 500 from Exxon Chemical Corporation of Baytown, Tex. and a nonwoven web of synthetic fibers such as is manufactured by Veratec Division of International Paper of Walpole MA under the designation DE 6957. Such laminates and means of producing them are described in the aforementioned U.S. Pat. No. 5,234,422. A preferred material for use as a support strip 32 comprises two plies of nonwoven material with a plurality of strands of elastic or an elastic scrim disposed therebetween. For example, one particularly preferred structure for the support strip comprises a first ply of a carded polypropylene nonwoven material having a basis weight of about 18 grams/square yard (21 grams/square meter), which is available from Fibertech Group, Inc., of Hopewell, N.J., a second ply of a spunbonded polypropylene nonwoven material having a basis weight of about 25 grams/square yard (30 grams/square meter), which is available from Fiberweb Group of Simpsonville, S.C., and four strands of LYCRA having a 620 decitex (grams per 10,000 meters), which is available from DuPont of Wilmington, Del., disposed therebetween to provide the requisite stretch modulus.

Alternatively, the support strip 32 may comprise a structural elastic-like film (SELF) web. A SELF web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. Thus, by controlling the relative sizes of the two regions described above, it is possible to provide a material having both the desired low stretch modulus and the desired extensibility. SELF webs suitable for the present invention are more completely described in commonly assigned U.S. Pat. No. 5,518,081 issued in the name of Chappell, et, al. on May 21, 1996, the disclosure of which is incorporated herein by reference.

Assembly of the Absorbent Structure

The components of the absorbent structure 20 such as the topsheet 24, the backsheet 26, the absorbent core 28, and any other components, may be assembled in a variety of well known configurations (including so called "tube" products or side flap products).

The components of the absorbent structure 20 are preferably assembled in a "sandwich" configuration with the topsheet 24, backsheet 26, and absorbent core 28 10 each comprising a layer and the absorbent core positioned between the topsheet 24 and backsheet 26. The topsheet 24 and the backsheet 26 are preferably joined about the periphery 23 using known techniques. The absorbent core 28 is also preferably joined to the backsheet 26 using known techniques. As described above, the support strip 32 is joined to the topsheet 24 along substantially its entire length while in an elongated state. The support strip 32 is also joined to the absorbent core 28 at attachment sites 34 while still in an elongated state. Similarly, as is also described above, the cuffs 40 are disposed on the body surface 24A of the topsheet 24 adjacent each longitudinal edge 22 and joined thereto in an elongated state. The components of the absorbent structure 20 can be secured together by adhesives, stitching, heat and/or pressure bonds, dynamic mechanical bonds, ultrasonic bonds, intermingling or entanglement of the fibers or other structural elements comprising the components of the sanitary napkin, such as by meltblowing the fibers comprising one component onto another component, extruding one component onto another, or by any other means known in the art.

Alternative Embodiments of the Present Invention

Decoupled Core

Figure 4:
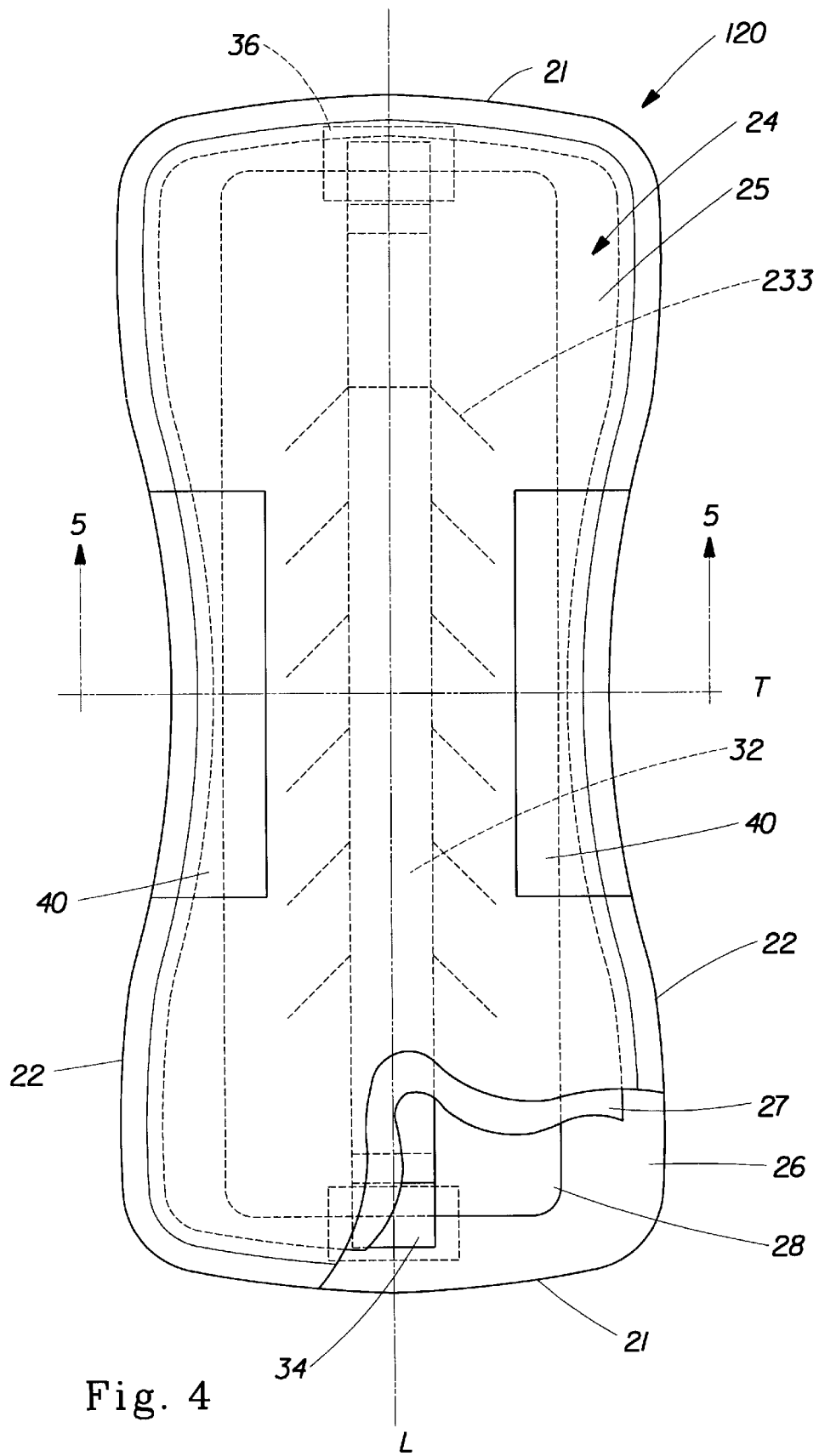
FIG. 4 is a top plan view of an alternative embodiment of the absorbent article of the present invention in flat out state with portions of the structure being cut-away to more clearly show the construction thereof.
Figure 5:
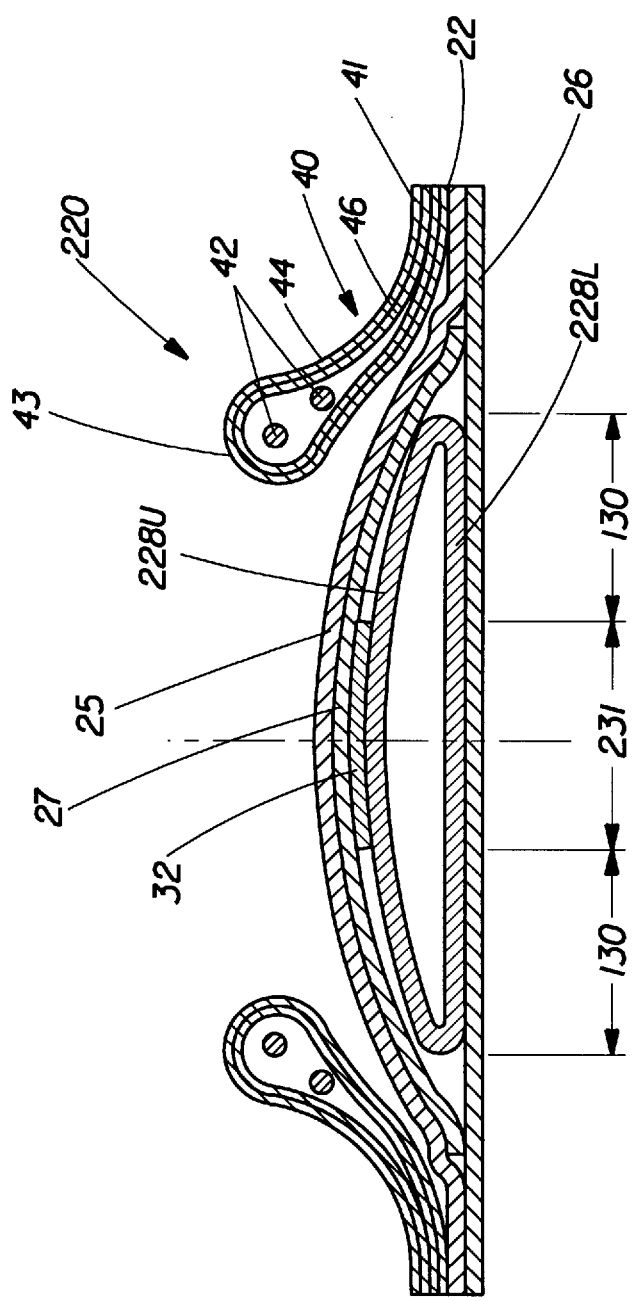
FIG. 5 is a transverse cross sectional view of the alternative embodiment of FIG. 4, with the topsheet, the support strip, and a portion of the absorbent core in a decoupled position.

In a first alternative embodiment of the present invention, absorbent structure 220 shown in FIGS. 4 and 5, a portion, upper ply 228U, of the absorbent core 228 is decoupled from the remainder of the core, lower ply 228L. The garment surface 32B of the support strip 32 is joined to upper ply 228U in central trisection 231 along that portion of the upper ply 228U that is provided with slits 233 (discussed below). The support strip 32 is joined to the lower ply 228L at attachment sites 34 as is shown in FIG. 3. In this alternative embodiment, the central trisection 231 is further provided with slits 233 in a pattern of longitudinally oriented, truncated chevrons as shown in FIG. 4. The slits 233 allow the central trisection 231 of the core 228, which is joined to the support strip 32 in the manner described above, to separate from the underlying ply 228L. That is, the pattern of slits facilitates the vertical separation of the plies when the upper ply 228U is lifted by the support strip 32. This places the upper ply 228U in close proximity to a wearer's pudendal region where it can draw bodily fluids away from the body surface 24A of the topsheet 24. The pattern of slits 233 also serves to direct bodily fluids in the longitudinal direction making more complete use of the absorbent capacity of the core 228. FIG. 5 shows the absorbent structure 220 in its decoupled position and demonstrates how the central trisection 231 separates from underlying components.

While the decoupled portion of the alternative absorbent structure 220 of the present invention has a greater caliper than the preferred embodiment due to the caliper of the upper ply 228U, this alternative embodiment conforms intimately to the shape of a wearer's body because the central trisection 231 of the upper ply 228U comprises only a single ply of tissue. As is shown in Table 2, the Lift of this alternative embodiment is at least 50% greater than the Lift of prior art absorbent articles in positions 1 and 2 of the Lift Test apparatus shown in FIGS. 10 and 11.

TABLE 2

| Product | Lift in Millimeters at Position | | |
|---|---|---|---|
|  | 1 | 2 | 3 |
| Preferred Embodiment of Present |  |  |  |
| Invention at 100% Prestretch | 23 | 17 | 18 |
| First alternative Embodiment of Present Invention at 100% Prestretch | 19 | 12 | 8 |
| Absorbent article of WO 95/20931* | 10 | 8 | 12 |

*Data from WO 95/20931

As noted above, positions 1 and 2 can be thought of as corresponding to a wearer's vaginal introitus and the perineum respectively. These results clearly demonstrate the excellent body fit of this alternative embodiment of the present invention.

Laterally Extending Flaps

In a second alternative embodiment of the present invention the absorbent structure 20 further comprises two opposing flaps (not shown) each of which are adjacent to and extend laterally from a longitudinal edge 22 of the absorbent core 28. The flaps are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet 24, backsheet 26, tissue, or combination of these materials. Further, the flaps may be a separate element attached to the main body of the absorbent structure 20 or can comprise extensions of the topsheet and backsheet (i.e., unitary). A number of sanitary napkins having flaps suitable or adaptable for use with absorbent structures of the present invention are disclosed in U.S. Pat. No. 4,687,478, which issued to Van Tilburg on Aug. 18, 1987; U.S. Pat. No. 4,589,876, which issued to Van Tilburg on May 20, 1986; and U.S. Pat. No. 4,608,047, which issued to Mattingly on Aug. 26, 1986. The disclosure of each of these patents is incorporated herein by reference.

Abbreviated Undergarment

In a third alternative embodiment, the present invention can take the form of an abbreviated undergarment 50. Such an undergarment is shown in plan view in FIG. 6. As can be seen therein, the undergarment 50 comprises a central absorbent portion 55 and an extensible shell portion 60. When the abbreviated undergarment 50 is worn, the central absorbent portion 55 has the same position as the crotch of a pair of panties. That is the central absorbent portion 55 is disposed between a wearer's legs and covers the wearer's pudendal region. The shell portion 60 serves to support the central absorbent portion 55 to help the central absorbent portion 55 maintain good body contact throughout the full range of wearer motion.

Central Absorbent Portion

In addition to fulfilling the functions of the crotch of a typical undergarment, the central absorbent portion 55 also receives and absorbs bodily fluids. The configuration of the central absorbent portion 55 is substantially the same as has been described above with respect to the absorbent structure 20. As a result, in discussing the central absorbent portion 55, elements having the same function in the central absorbent portion 55 as a corresponding element in the absorbent structure 20 discussed above will be identified with the same reference number.

The central absorbent portion 55 comprises a liquid pervious topsheet 24, a liquid impervious backsheet 26 joined with the topsheet 24, an absorbent core 28 positioned between the topsheet 24 and the backsheet 26, and support strip 32 which is disposed between the topsheet 24 and the absorbent core 28. The central absorbent portion 55 also comprises a pair of longitudinally extending cuffs 40 and a secondary topsheet layer 27. Because the central absorbent portion 55 is supported by the shell portion 60 rather than by a wearer's undergarment, the central absorbent portion 55 does not require attachment means 36. This portion of the abbreviated undergarment 50 is shown clearly in FIGS. 1–3 and will not be described further in the spirit of brevity.

Extensible Shell Portion

The extensible shell portion 60 of the abbreviated undergarment 50 embodiment of the present invention serves to support and lift the central absorbent portion 55 to help it maintain good bodily contact throughout the full range of wearer motions. As such, the shell portion is resilient (i.e. elastically extensible) in at least the longitudinal direction. Preferably, the shell portion is elastically extensible in both the lateral and the longitudinal directions. Such elastic extensibility enables the abbreviated undergarment 50 to fit a variety of bodily shapes and sizes and provides good conformity to a wearer's body. An elastically extensible shell portion 60 further co-operates with the central absorbent portion 55 to provide a "z-direction" biasing force to the central absorbent portion 55 throughout the full range of wearer movement. Such a biasing force helps maintain the central absorbent portion 55 in close bodily contact, particularly with a wearer's pudendal region. Preferably, the shell portion 60 is constructed so as to provide a stretch modulus of between about 150 (g/cm)/% and about 200 (g/cm)/%. More preferably the stretch modulus is between about 160 (g/cm)/% and about 180 (g/cm)/%. A suitable method for measuring stretch modulus is described in the TEST METHODS section below.

In a particularly preferred embodiment, the shell portion 60 is breathable so the abbreviated undergarment 50 is comfortable to wear. As used herein, a material is "breathable" if the air permeability of the material is greater than about 25 cubic feet per minute per square meter (0.7 cubic meters per minute per square meter) when measured as described in the TEST METHODS section below. Preferably, the air permeability of the shell portion 60 is greater than about 220 cubic feet per minute per square meter (6.5 cubic meters per minute per square meter). More preferably, the air permeability of the shell portion 60 is greater than abiout 300 cubic feet per minute per square meter (8.5 cubic meters per minute per square meter).

The shell portion 60 is compliant, soft feeling, and non-irritating to a wearer's skin. A suitable shell portion 60 may be manufactured from woven, knit, or nonwoven materials or combinations thereof as long as the shell portion 60 has the requisite stretch modulus. For example, the shell portion 60 may comprise a material knit from strand materials (e.g. yarns), wherein at least a portion of the strand materials are elastically extensible. Preferably, however, the shell portion 60 comprises an elastically extensible laminate of a nonwoven material and an elastically extensible member. While a laminate of a nonwoven material and an elastically extensible film material is suitable for use as a shell portion 60, a preferred laminate for the shell portion 60 comprises a nonwoven material and an elastically extensible strand material or an elastically extensible scrim material. Such laminates are preferred because they are breathable, while a laminate that comprises an elastically extensible film material would not be breathable.

Figure 6:
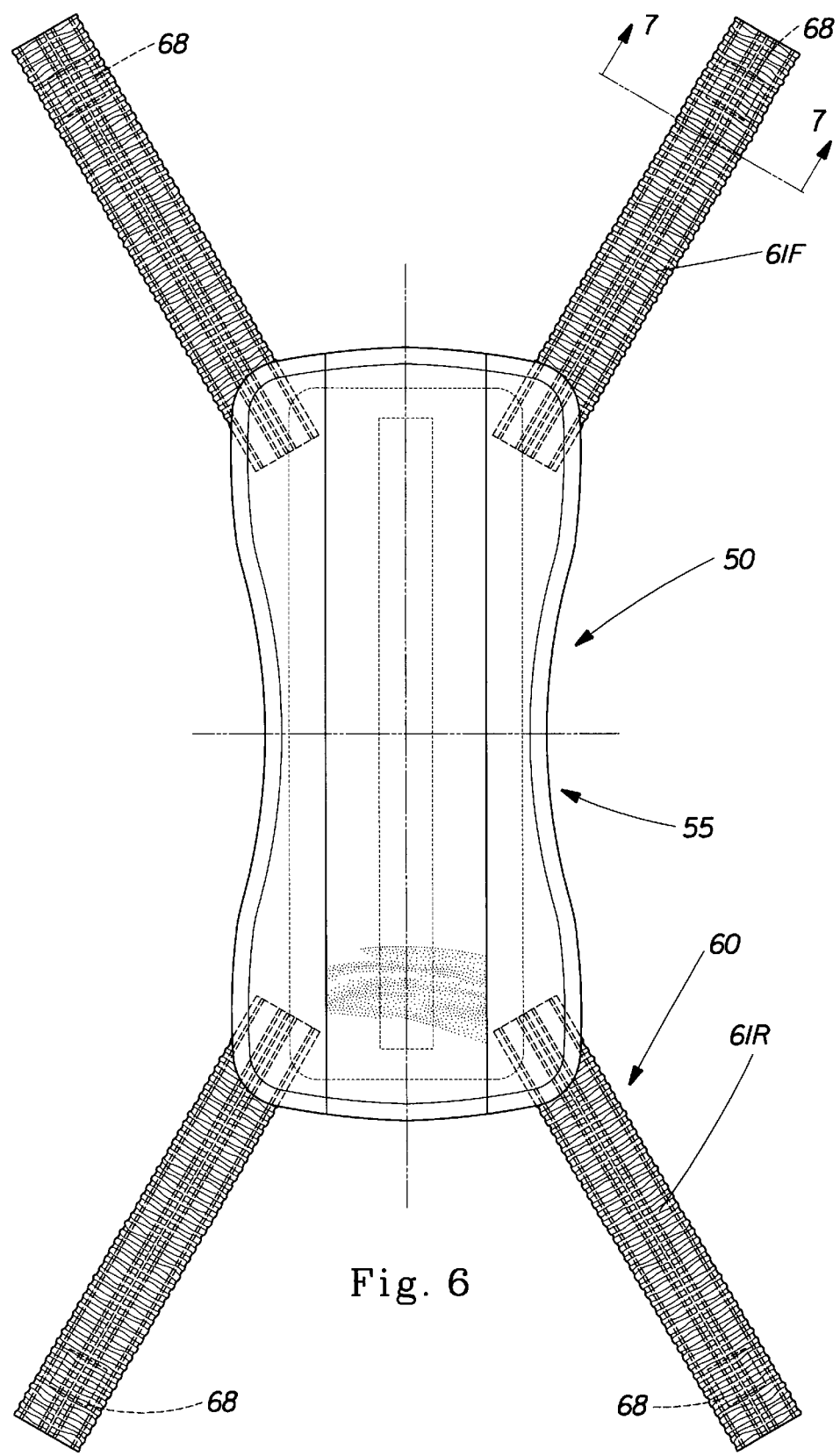
FIG. 6 is a top plan view of an alternative, abbreviated undergarment embodiment of the present invention.
Figure 8:
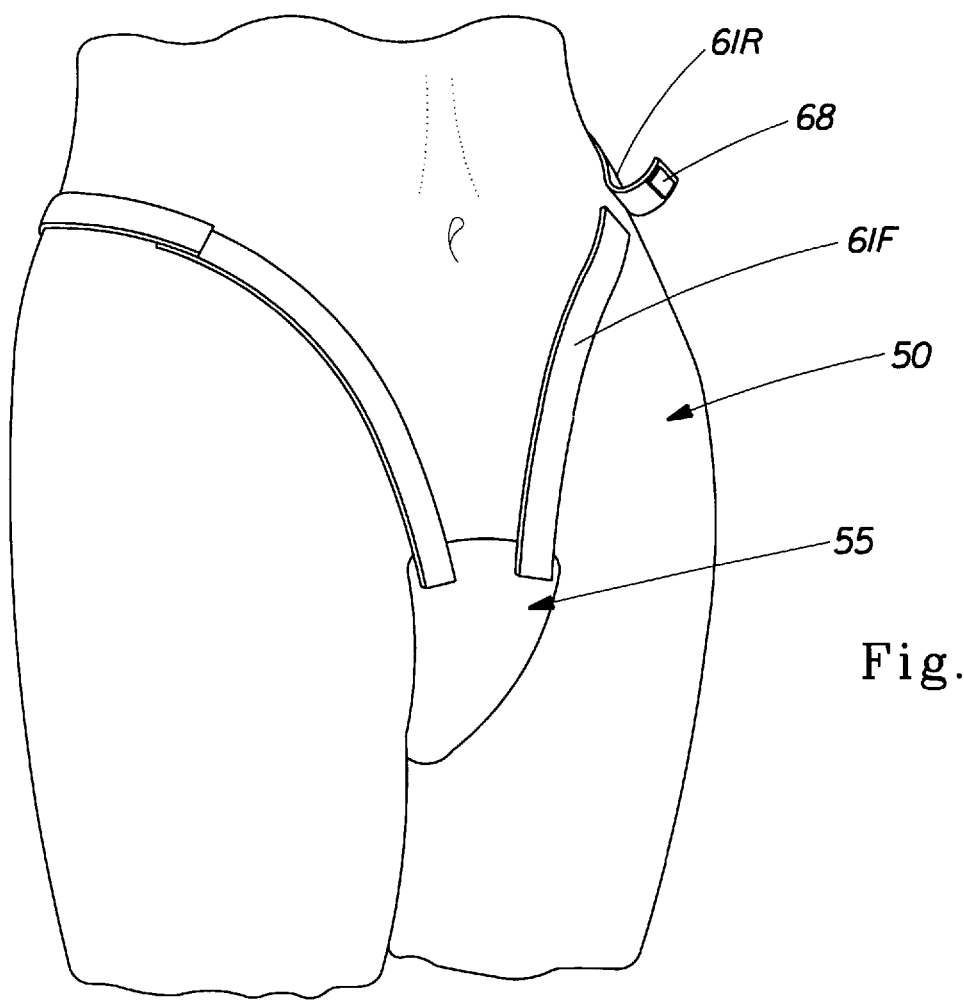
FIG. 8 is perspective view showing the abbreviated undergarment embodiment of the present invention being worn.

As can be seen in FIG. 6, the shell portion 60 preferably comprises a pair of elasticized front straps 61F and a pair of elasticized rear straps 61R. Each strap has a proximal end that is joined to the absorbent portion 55 adjacent an end edge 21 thereof Each strap 61 also has a distal end which, as can be seen in FIG. 8, wraps around a wearer's hips and, when a front strap 61F is joined to a rear strap 61R, insures that the shell portion 60 supports the central absorbent portion 55.

Figure 7:
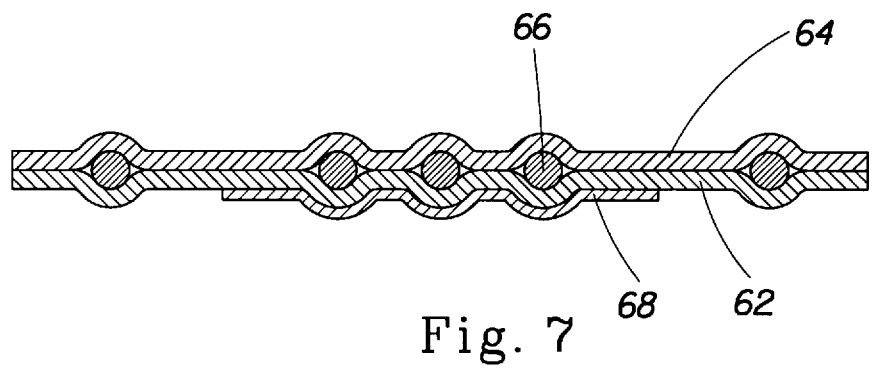
FIG. 7 is a cross sectional view taken along line 7—7 of FIG. 6.

A front strap 61F is shown in cross section FIG. 7. The cross section of the rear straps 61R is identical. As can be seen in FIG. 7, the strap 61F comprises first and second fabric members 62 and 64 with a shell elastic member 66 disposed therebetween and joined thereto in an elastically extended state. While the first and second fabric members 62, 64 can comprise different materials if a particular need dictates, they preferably comprise separate lamina of the same material.

Each strap 61 is fabricated in a manner similar to that used to fabricate the cuffs 40. That is the shell elastic member 66 is elongated to at least between about 100% and about 400% of its relaxed length, preferably between about 150% and about 350%, more preferably about 250%. The elongated shell elastic member 66 is then disposed on the first fabric member 62 and joined thereto. The second fabric member 64 is then disposed on the first fabric member 62 and the elongated shell elastic member 66 and joined thereto using means known to the art (not shown) to form a laminate. For example, adhesive means as described above for joining the backsheet 26 to the absorbent core 28 could be used. The distal end of each strap is then joined to the central absorbent portion 55 adjacent an end edge 21 thereof.

Suitable materials for the shell elastic member 66 include strands, ribbons, a film, or a composite material. Particularly preferred are strands, preferably five strands for each strap 61. The strands may be of any suitable elastomeric material. One suitable material is spandex, such as LYCRA, which is available from DuPont of Wilmington, Del. Preferred LYCRA strands have a decitex of about 3760.

The first and second fabric members 62, 64 can comprise the same or different materials. Preferably, the first and second fabric members 62, 64 comprise the same material. Suitable materials include woven and nonwoven materials having a comfortable hand and sufficient porosity for wearer comfort. Particularly preferred are nonwoven materials. A suitable nonwoven material is DE 6957 from Veratec which is described above with respect to the support strip 32.

The shell portion 60 also comprises strap attachment means 68 disposed thereon. Such strap attachment means 68 are used to join the distal ends of the straps 61F, 61R to each other to such that the straps 61F, 61R wrap around a wearer's hips and support central absorbent portion 55 against a wearer's pudendal region thereby (The abbreviated undergarment 50 embodiment of the present invention is shown in an in-use condition in FIG. 8). Such attachment means can comprise attachment means known to those skilled in the art including adhesive fastening systems, cohesive fastening systems and mechanical fastening systems.

A particularly preferred attachment means 68 is a mechanical fastening system comprising a male component (i.e. an engaging element) and a female component (i.e. a receiving element). The term "male component", as used herein, is used to designate the portion of the strap attachment means 68 having engaging elements such as hooks. The term "female component", as used herein, is intended to designate the portion of the strap attachment means 68 that is engaged by the male component.

Male fastening components may include conventional, commercially available hook materials, but are not limited to such conventional hooks. For example, the engaging elements may have any shape known in the art such as hooks, "T's", mushrooms, prongs or any other shape. Further, the male component may be manufactured from a wide range of materials. Such suitable materials include, but are not limited to, nylon, polyester, polypropylene, or any combination of these or other materials. One suitable male component may comprise a number of shaped engaging elements projecting from a woven backing such as the commercially available material designated "SCOTCHMATE" brand No. FJ3402 available from Minnesota Mining and Manufacturing Company, St. Paul, Minn. Another suitable male component is described in U.S. Pat. No. 4,846,815, which issued to C. L. Scripps on Jul. 11, 1989. Other suitable male components and methods for making the same are the prongs described in U.S. Pat. No. 5,058,247 issued to Thomas et al. on Oct. 22, 1991; U.S. Pat. No. 5,116,563, which issued to Thomas et al. on May 26, 1992; U.S. Pat. No. 5,180,534, which issued to Thomas, et al. on Jan. 19, 1993; and U.S. Pat. No. 5,230,851, which issued to Thomas on Jul. 27, 1993. The disclosure of each of these patents is hereby incorporated by reference herein.

The female component may include commercially available loop materials as are known for such hook and loop fastening systems but are not limited to such materials. Suitable female components include reticulated foams, knitted fabrics, nonwoven materials, and stitchbonded loop materials, such as Velcro brand loop materials sold by Velcro USA of Manchester, N.H. A suitable female component is stitchbonded fabric Number 970026 sold by the Milliken Company of Spartanburg, S.C.

A wearer would use the abbreviated undergarment 50 of the present invention by placing the central absorbent portion 55 between her legs, drawing an opposing pair of straps 61F, 61R about a first hip and joining the distal ends thereof using strap attachment means 68, and drawing the remaining opposing pair of straps 61F, 61R about her other hip and joining the distal ends thereof in a like manner.

Figure 9:
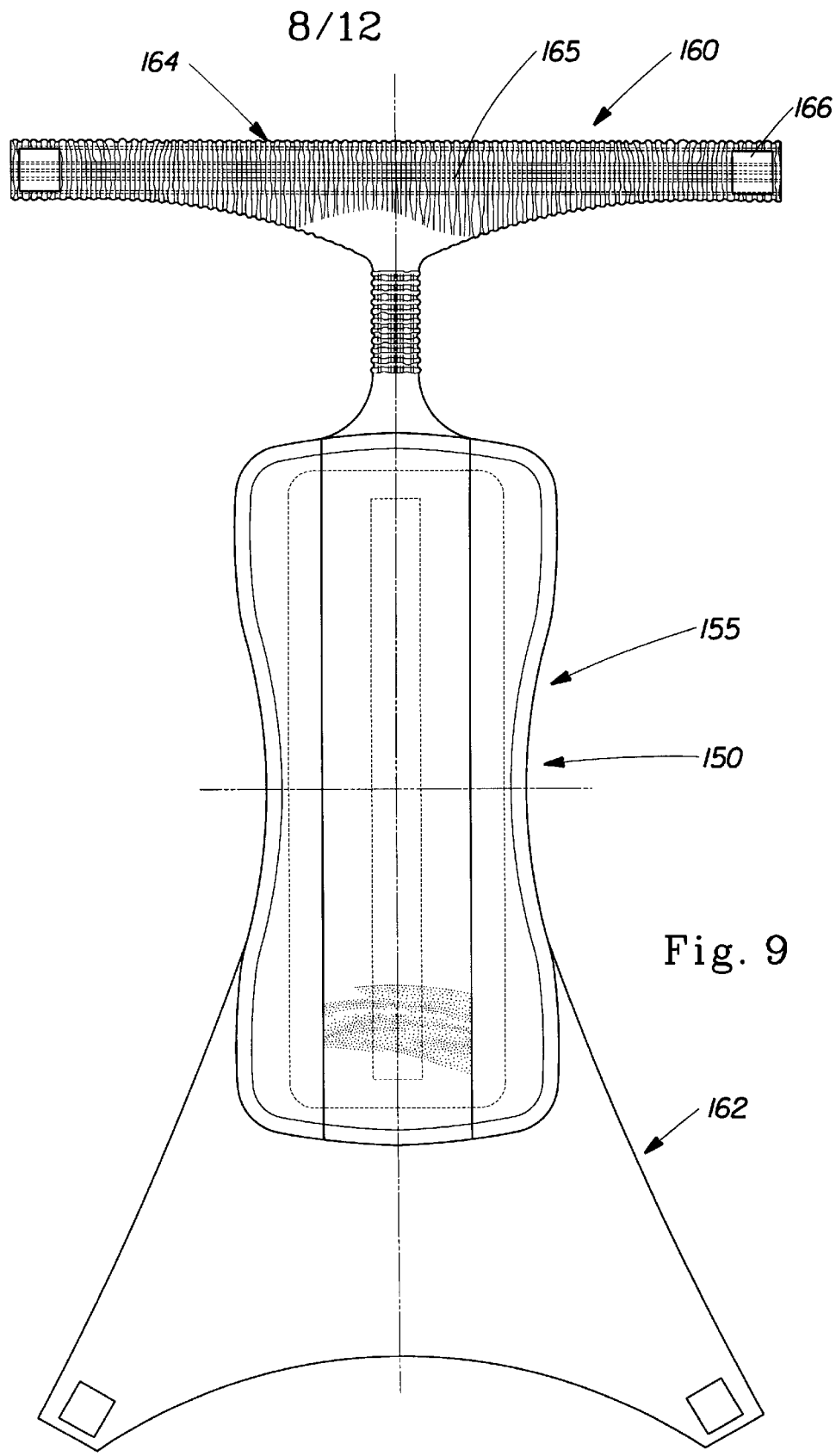
FIG. 9 is a a plan view of an alternative embodiment of the abbreviated undergarment form of the present invention.

An alternative structure for the abbreviated panty 150 is shown in FIG. 9. One of ordinary skill in the art will recognize that the key performance criterion for such an alternative structure is that it supports and lifts the central absorbent portion 155 to help it maintain good bodily contact throughout the full range of wearer motions. As can be seen in FIG. 9 the shell portion 160 comprises a front portion 162 and a rear portion 164. Front portion 162 has a shape similar to the shape of the front panel of a pair of "bikini" briefs. Such shape provides additional coverage of a wearer's body (i.e. additional discretion when the abbreviated panty 150 is worn). The rear portion 164 has a "T" configuration. The bars of the "T" 165 form the rear part of a waistband when the front shell portion 162 is joined to the rear shell portion 164 using waist attachment means 166. The upright of the "T" provides the additional benefit of directing a lifting force through a wearer's gluteal groove so as to improve the seal against the wearer's perineum.

One of ordinary skill in the art will recognize that additional embodiments of the shell portion are possible as long as such embodiments provide sufficient support to keep the central absorbent portion in good bodily contact.

TEST METHODS

Lift Test

Introduction

This test involves the use of a lift measuring test apparatus that is shaped to roughly approximate the various areas of a female body that the absorbent article must fit adjacent in order to achieve close body contact. The lift measuring test apparatus comprises two curved PLEXIGLAS pieces that are intended to approximate the portions of the wearer's body that the crotch of the wearer's undergarments contact during wear. The apparatus contains longitudinally-oriented slit-like opening that is intended to approximate the space between the wearer's labia and the crevice between the wearer's buttocks (the "gluteal groove"). The ends of the absorbent article are attached to clamps which are adjusted to simulate the forces exerted when a woman's panties are pulled up to the wearer's body. The distance that the middle of the absorbent article vertically intrudes into the slit-like opening is measured to provide a relative measurement of body contact.

Apparatus

Lift Measuring Apparatus The lift measuring test apparatus comprises six pieces of PLEXIGLAS arranged as shown in FIGS. 10–15. The Lift Test apparatus 100 has an inside surface 100A, an outside surface 100B, a front portion 100C, and a rear portion 100D.

Figure 10:
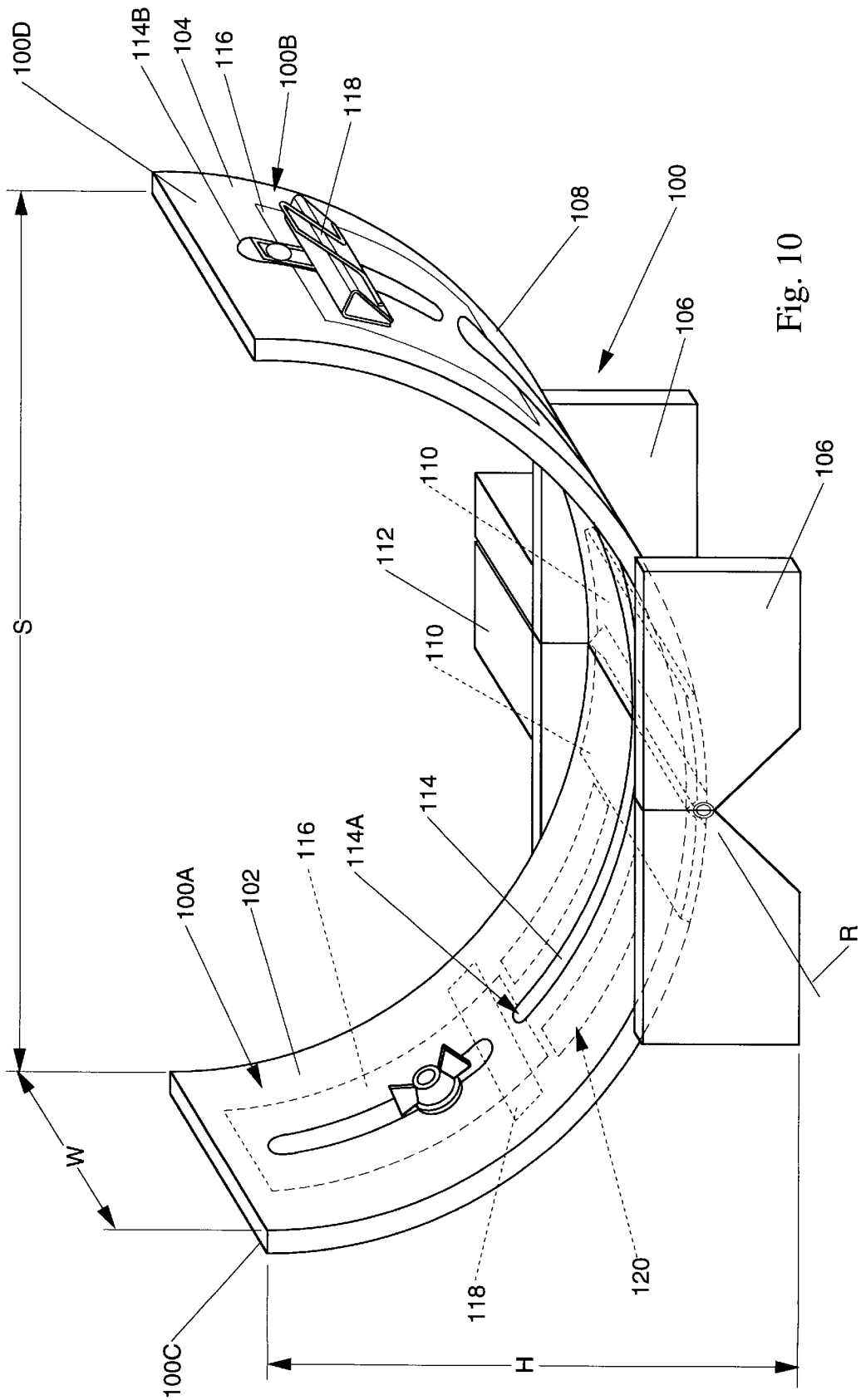
FIG. 10 is a perspective view of the Lift Test apparatus.
Figure 11:
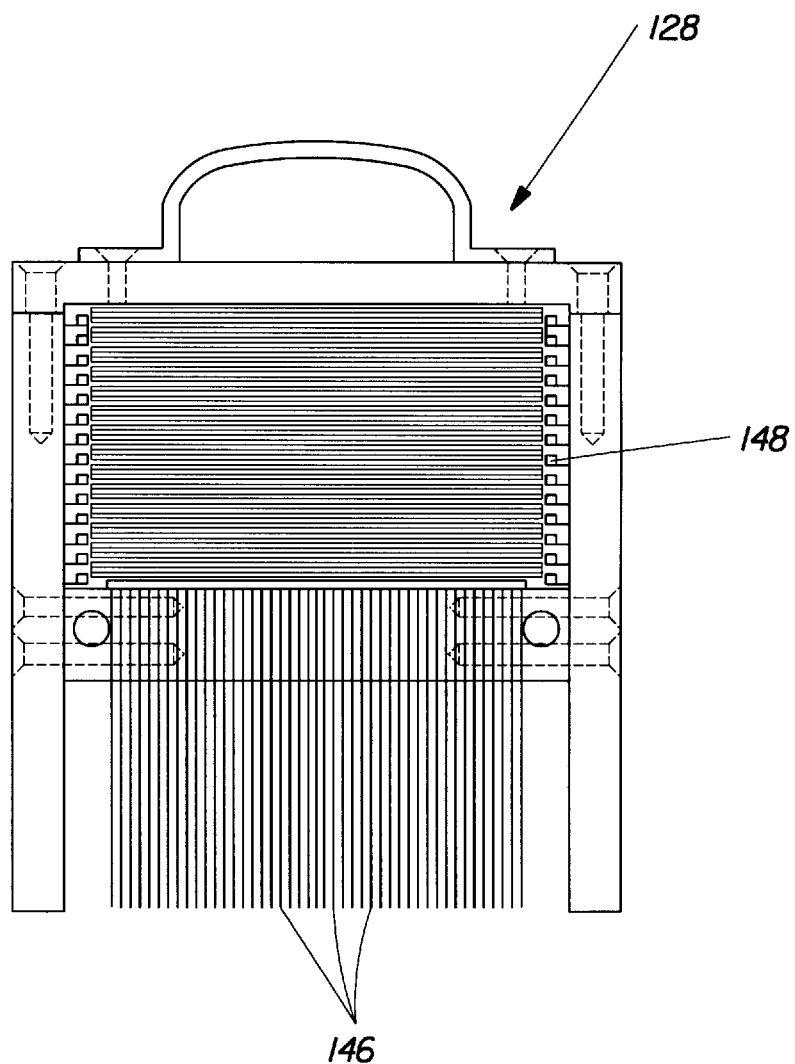
FIG. 11 is a front view of the Pin Chamber caliper measurement device used in the Lift Test.
Figure 12:
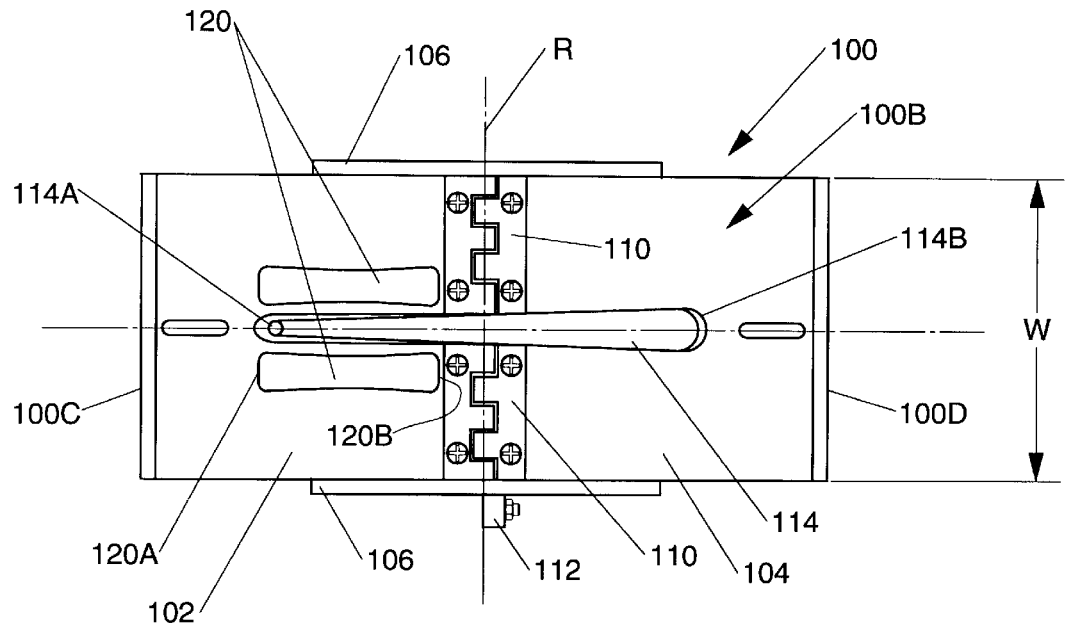
FIG. 12 is a bottom view of the Lift Test apparatus.
Figure 13:
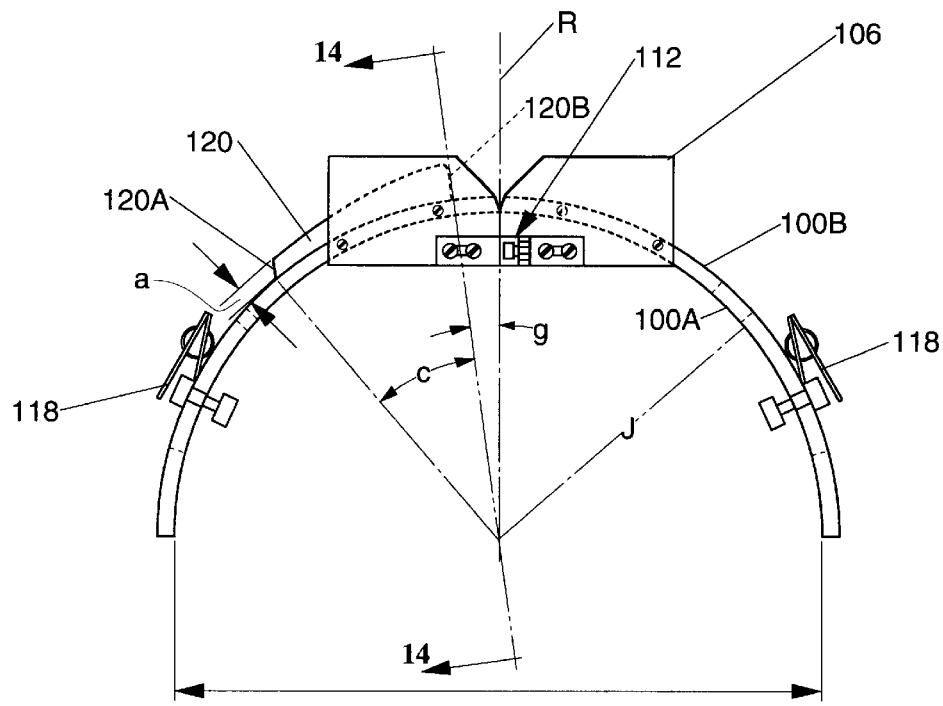
FIG. 13 is a side view of the Lift Test apparatus.

The PLEXIGLAS pieces include two identical ¼" thick arcuate pieces 102 and 104 which have a height H of 150 mm, a width W of 135 mm, a length S of 300 mm when assembled in an abutting relationship as shown in FIGS. 10–12, and a radius of curvature of the inner surface of the arcuate pieces, J (as shown in FIG. 12), of 150 mm. A pair of rectangular PLEXIGLAS support legs 106 are mounted on the sides of the arcuate PLEXIGLAS pieces as shown in FIG. 10. The support legs 106 are mounted perpendicularly to the arcuate pieces so that the bottom 108 of the arcuate pieces is held at least 20 mm above the table on which the test apparatus 100 is placed.

The arcuate pieces 102 and 104 are connected by a pair of hinges 110 that allow the arcuate pieces to open 90°. The arcuate pieces 102 and 104 are held together at the transverse centerline R of the test apparatus by a magnet 112 when closed. The arcuate pieces have an 8 ⅜ inch (212 mm) long central longitudinally-oriented slit-like opening (or "slit") 114 (as measured along the curvature of the outside surface 100B of the arcuate pieces) that varies linearly in width from 6 mm at the portion 114A of the slit located nearest to the front of the portion 100C of the test apparatus (the portion of the apparatus that is intended to represent the front of the wearer's body) to 19 mm at the portion 114B of the slit located nearest to the rear 100D of the apparatus. The portions of the PLEXIGLAS surrounding the slit 114 are beveled at a 45° angle so that the slit is wider on the bottom surface 100B than on the top surface of the arcuate pieces. Both ends of the slit 114 are rounded.

The arcuate pieces have additional channels to the front and rear of the slit 114 which are oriented along the longitudinal centerline of the slit. These channels provide a mechanism within which the bolts holding the clamps 118 can slide to adjust the position of the clamps relative to the slit. The arcuate pieces 102 and 104 are provided with tape 116 which can be marked with indicia to indicate the proper position for clamping the ends of the absorbent article in clamps 118.

The front arcuate piece 102 of the test apparatus is also provided with a pair of three-dimensionally curved PLEXIGLAS pieces 120 that are intended to represent the wearer's labia majora. The curved pieces 120 have the configuration shown in FIGS. 11–13 and the dimensions shown in Table 3 below. The curved pieces are centered about the slit and are spaced 36 mm apart (on center) as described in Table 3 and their rear end edges 120B are spaced from the rear end edge of the first arcuate plate 102 that is defined by the 8° angle g described in Table 3.

TABLE 3

Dimensions of Curved Pieces

| Dimension | Size (in mm) |
|---|---|
| a | 7 mm |
| b | 16 mm |
| c | 33 degrees |
| d | 16 mm |
| e | 6 mm (radius) |

TABLE 3-continued

Dimensions of Curved Pieces

| Dimension | Size (in mm) |
|---|---|
| f | 36 mm |
| g | 8 degrees |
| Weights | Sufficient weight to place total weight of 314 grams on the sample (including weight of clamps (described below)). |
| Clamps | 2 spring-loaded, finger-operated 2 inch (5 cm) wide clamps (Boston No. 2 clips manufactured by Hunt Manufacturing Co., Statesville, N.C.) for securing the absorbent article in the test apparatus using bolts with wing nuts. |
| Pin Chamber Caliper Measurement Device | Constructed according to attached drawing FIG. 11. |

Procedure

The release paper covering any adhesive fastener on the garment-facing side of the absorbent article is removed prior to the beginning of the test and any fastener is covered such as by sprinkling talc on adhesive fasteners to minimize the effect of the fastener on the test results. (Unless otherwise stated, this applies to all test procedures described in this specification.)

The caliper of the absorbent article is first measured. Two caliper measurements are taken. The caliper of the point of maximum amplitude of the absorbent article is measured. A measurement of the portion of the absorbent article having the smallest caliper which contains absorbent material is also taken (i.e., the minimum caliper). The maximum and minimum calipers are determined by taking a sufficient number of caliper measurements at different places over the absorbent article to ensure that the caliper of the portion of the absorbent article with the largest and smallest calipers are measured.

The amount that the absorbent article will extend under a 314 gram force (or other force as desired) is then measured. This is done to calibrate the test apparatus for each different type of absorbent article being tested. The absorbent article used for the caliper measurements is discarded and a separate absorbent article is used for this measurement. The second absorbent article sample is placed with the body-facing side 20A of the absorbent article 20 adjacent to the outside surface 100B of the arcuate PLEXIGLAS plates of the testing apparatus as shown in FIG. 14A. The absorbent article, unless it is provided with flaps or side wrapping elements that are offset forward or rearward of the main body of the article, is centered longitudinally with respect to the transverse centerline R of the test apparatus. If the absorbent article has flaps which are offset, the absorbent article is centered on the arcuate plates so that the flap (or side wrapping elements) transverse centerline coincides with the transverse centerline R of the test apparatus.

The clamp 118 at the front portion 100C of the test apparatus is set so that the edge of the jaw of the clamp is spaced 150 mm from the transverse centerline R of the test apparatus (as measured along the curvature of the inside surface 100A of the test apparatus. The clamp 118 at the rear portion 100D of the test apparatus is initially spaced the same distance from the transverse centerline R of the apparatus (toward the rear portion of the test apparatus).

A piece of tape is prepared for each end of the absorbent article. The tape comprises a folded one inch wide strip of 3M masking tape available from the Minnesota Mining and Manufacturing Company of St. Paul, Minn. The strip is folded lengthwise as shown in FIG. 15 so that it extends the desired overall length and all but a one inch (2.54 cm) by ½ inch (1.3 cm) area of the adhesive is covered at one end. The tape is used to equalize the results for absorbent articles having different lengths and to negate the effect of the different length and position of the fasteners on the garment side of the article.

A first folded piece of tape is made a length that is long enough so that its exposed adhesive section can be affixed to the front end of the absorbent article in the manner described below and the other end of the tape can be gripped by the clamp at the front portion of the test apparatus while the absorbent article is centered over the test apparatus.

The end of the first folded piece of tape is adhered to the garment-facing side of the absorbent article. The end of the tape with the exposed adhesive is adhered to the absorbent article so that it is centered along the longitudinal centerline of the absorbent article The end of the exposed adhesive section nearest the end of the tape that will go in the clamps aligns with the most longitudinally remote edge of the fastener on the garment-facing side of the absorbent article as shown in FIG. 15. If the absorbent article is not provided with a fastener on its garment-facing side, then the exposed adhesive section of the first piece of tape is adhered to the garment-facing side of the absorbent article a similar distance inward from the portion of the garment-facing side that overlays the end edge of the absorbent material of the absorbent article. Thus, in FIG. 15, the line u denotes either the end edge of a fastener or the end edge of the absorbent material of the absorbent article.

The second folded piece of tape is adhered to the garment-facing side of the absorbent article and clamped in the same manner as the first piece of tape. The other end of the piece of tape is gripped in the clamp 118 at the adjacent end of the test apparatus. The nut on the clamp 118 at the front portion 100C of the test apparatus is tightened. The nut on the clamp 118 at the rear portion 100D of the test apparatus is left loose so that it can slide freely.

Weights 124 are hung from the clamp 118 at the end of the absorbent article at the rear portion of the test apparatus (where the nut has been loosened). The weight is allowed to hang freely (although a short length of the wire 122 holding the weight 124 may contact part of the rear portion 100D of the test apparatus as shown in FIG. 14A). The weight should not be dropped, nor should a sudden force be applied with the weight when the pad is hanging freely. After a period of 5 seconds the nut on the clamp at the rear portion 100D of the test apparatus is tightened.

The weight on the end of the absorbent article at the rear portion of the test device places a stretching force on the absorbent article so that the absorbent article tends to want to form a straight path between the clamps. At this point, the absorbent article will move into as close contact within the slit as the absorbent article is capable of achieving under the test conditions.

The test apparatus 100 is turned right side up so that it rests on its support legs 106. The Pin Chamber caliper measurement device is then used to measure the distance the absorbent article rises within the slit from the outside surface 100B of the arcuate plates (the baseline).

The Pin Chamber 128 comprises a case with a plurality of narrow (1.1 mm diameter), spaced apart, vertically-oriented, lightweight (28.4 mg) pins 146 arranged in a row across the device. The pins are movable in the vertical direction. The Pin Chamber case has a glass window in the front and back so that the height of the pins can be observed when the Pin Chamber is in use. A ruler 148 marked in millimeter increments is provided along side of the pins prior to the placement of the absorbent article on the test apparatus. The Pin Chamber is positioned over the test apparatus so that it straddles the test apparatus. A measurement to determine the distance the pins drop to the bottom surface of the arcuate plates is taken at each of the desired locations. These measurements serve as the baseline values for the test. The distance the pins drop above or below the baseline is then measured by gently lowering the pins with the absorbent article in place. It should be noted that the slit is wide enough that several pins may drop between the edges of the slit at various locations. If that occurs, the reading taken is that of the highest pin.

The first measurement is taken at a point that is spaced 47 mm forward of the transverse centerline R of the test apparatus. This distance is intended to correspond with the labia area of wearer's body. (This 47 mm distance, and the following two distance measurements are measured along the curvature of the inside surface 100A of the test apparatus.) The second measurement is taken at a point that is spaced 17 mm to the rear of the transverse centerline of the test apparatus. This is intended to correspond with the wearer's perineum. The third measurement is taken at a point that is spaced 70 mm to the rear of the transverse centerline of the test apparatus. This is intended to correspond with the wearer's "gluteal groove". These values are recorded. The foregoing procedure is repeated for a total of three representative absorbent articles. The three measurements obtained are then averaged to provide a value for the Lift of the absorbent article at each of the locations.

Stretch Modulus

Intent

This method is intended to quantify a force comparable to the force exerted on a wearer's body by elastically extensible materials.

Method

The method described in INDA (Association of Nonwoven Fabric Industry) Standard Test 110.1-92 is suitable. The following set up conditions are used:

Gage Length: 6 inches (5.08 centimeters) For samples having a length unsuitable for a 6 inch (5.08 centimeter) gage length, measure and record the gage length necessary to securely attach the sample to the tensile testing machine. Percent elongation is calculated as follows:

% Elongation=(Jaw Separation–Gage Length)/(Gage Length)

Crosshead Speed: 20 inches/minute (50.8 centimeters/minute)

Tensile Testing Machine: Appropriate for expected force range, a Model and Load Cell Type 5564, available from Instron Corporation, Canton, Mass. is suitable Sample Width: 1 inch (2.54 centimeters) For samples different than 1 inch (2.54 centimeters) wide, measure the sample width and adjust the measured force by the ratio of 1 inch (2.54 centimeters) to the measured width.

Sample Size: At least three samples per material tested

Calculations $Force_{40}$: Force at 40% elongation (grams/inch or grams/cm)

$Force_{60}$: Force at 60% elongation (grams/inch or grams/cm)

Stretch Modulus=$(Force_{60}-Force_{40})/0.20$ ((g/inch)/% or (g/cm)/%)

Report the mean and standard deviation for stretch modulus

Air Permeability

Intent

This method is intended to measure the flow of air through a material at a defined pressure drop across the material.

Apparatus

Air permeability tester, available from Albany International Corporation of Albany N.Y.

Sample Preparation

1. Cut the sample into an approximate 4 inch×4 inch (10 centimeter×10 centimeter) square.

Method

Operate the air permeability tester according to the manufacturer's instructions. The following briefly summarizes the operating procedure described therein.

1) Mount the sample by stretching it sufficiently taut over the outer orifice plate to remove any distortions that may impede or distort the air flow. The sample is mounted such that the less open side, if the sample is determined to have such, faces toward the mounting plate.
2) Determine the appropriate inner orifice to provide the proper air flow for the sample being tested. Record the number of the orifice plate used for evaluating the sample.
3) Adjust the fan motor speed to provide a pressure drop of 0.5 inches of water (1.27 centimeters of water)across the inner orifice.
4) Record the pressure drop across the sample.

Calculation and Report

Using the tables provided by the manufacturer, the orifice plate number and the pressure drop across the sample, determine the air flow through the sample. Report the mean and standard deviation for each sample evaluated.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent structure for absorption of bodily fluids discharged by a female wearer, the disposable absorbent structure having a longitudinal centerline defining a longitudinal direction, a lateral centerline defining a lateral direction, longitudinally oriented side edges, and laterally oriented end edges, wherein said side edges and said end edges define a periphery for said absorbent structure, said absorbent structure comprising:

a liquid impervious backsheet having longitudinally oriented side edges and laterally oriented end edges, said side edges of said backsheet being juxtaposed with said side edges of said absorbent structure and said end edges of said backsheet being juxtaposed with said end edges of said absorbent structure;

an absorbent core having longitudinally oriented side edges and laterally oriented end edges disposed on and joined to said backsheet, wherein said side edges and said end edges of said backsheet extend outward from said side edges and said end edges of said absorbent core;

a liquid pervious topsheet having longitudinally oriented side edges and laterally oriented end edges disposed on said absorbent core, wherein said side edges and said end edges of said topsheet extend outward from said side edges and said end edges of said absorbent core and are joined to said backsheet about said periphery thereby enclosing said absorbent core; and an elastically extensible, longitudinally oriented support strip having laterally oriented ends which is disposed along said longitudinal centerline between said absorbent core and said topsheet, wherein said ends of said support strip are joined to said absorbent core adjacent said end edges of said absorbent structure such that said support strip provides an elastic contractive force which causes at least a portion of said support strip and at least a portion of said topsheet to vertically separate from said absorbent core.

2. An absorbent article for wearing in an undergarment, said absorbent article having a longitudinal centerline and a periphery and comprising:

a liquid impervious backsheet;

a liquid pervious topsheet joined to said backsheet at least about said periphery;

an absorbent core disposed between said backsheet and said topsheet, said absorbent core having longitudinally oriented side edges and laterally oriented end edges, wherein said side edges and said end edges of said absorbent core lie inboard of said periphery; and lifting means disposed alone said longitudinal centerline, said means causing said absorbent article to have a Lift of greater than about 19 mm at a first position when positioned in a Lift Test Apparatus, said Test Apparatus comprising an arcuate plate with a slit at the bottom of said arcuate plate which slit is 212 mm long, and varies in linearly width from 6 mm at the front to 19 mm at the rear, said first position being located 47 mm forward of a transverse centerline of said Test Apparatus, said absorbent article having said Lift when it is clamped in said Test Apparatus and a weight of 314 grams is applied to the end of the absorbent article at the rear of said Test Apparatus.

3. The disposable absorbent structure of claim 1 wherein said support strip comprises an elastic member.

4. The disposable absorbent structure of claim 3 wherein said elastic member comprises an elastic scrim material.

5. The disposable absorbent structure of claim 3 wherein said elastic member comprises a plurality of elastic strands.

6. The disposable absorbent structure of claim 1 wherein said support strip comprises a laminate of a nonwoven material and an elastic member.

7. The disposable absorbent structure of claim 6 wherein said elastic member comprises an elastic scrim material.

8. The disposable absorbent structure of claim 6 wherein said elastic member comprises a plurality of elastic strands.

9. The disposable absorbent structure of claim 6 wherein said nonwoven material comprises a carded nonwoven.

10. The disposable absorbent structure of claim 6 wherein said laminate comprises two plies of nonwoven material and said elastic member is disposed between said two plies of nonwoven material.

11. The disposable absorbent structure of claim 10 wherein said two plies of nonwoven material comprise a first ply comprising a first nonwoven material and a second ply comprising a second nonwoven material.

12. The disposable absorbent structure of claim 10 wherein said two plies of nonwoven material comprise the same material.

13. The disposable absorbent structure of claim 11 wherein said first nonwoven material comprises a carded nonwoven and said second nonwoven material comprises a spunbonded nonwoven.

14. The disposable absorbent structure of claim 1 wherein said absorbent structure further comprises a pair of laterally opposed, longitudinally extending cuffs, wherein a cuff is disposed on said topsheet adjacent each of said side edges thereof.

15. The disposable absorbent structure of claim 1 wherein said support strip is further joined to said absorbent core such that at least a portion of said absorbent core also vertically separates from the remaining portion of said absorbent core.

16. The disposable absorbent structure of claim 15 wherein said absorbent core comprises a first ply and a second ply wherein said first ply overlies said second ply and said first ply is provided with a pattern of slits, said pattern of slits facilitating said vertical separation of said first ply relative to said second ply.

17. The disposable absorbent structure of claim 1 wherein said topsheet is provided with a treatment for drawing fluids therethrough.

18. The disposable absorbent structure of claim 17 wherein said treatment comprises flocking.

19. A disposable absorbent structure for absorption of bodily fluids discharged by a female wearer, said disposable absorbent structure having a longitudinal centerline defining a longitudinal direction and a lateral centerline defining a lateral direction, said absorbent structure comprising:

a liquid impervious backsheet having longitudinally oriented side edges and laterally oriented end edges defining a periphery for said absorbent structure;

an absorbent core having longitudinally oriented side edges and laterally oriented end edges disposed on and joined to said backsheet, wherein said side edges and said end edges of said backsheet extend outward from said side edges and said end edges of said absorbent core;

a liquid pervious topsheet having longitudinally oriented side edges and laterally oriented end edges disposed on said absorbent core, wherein said side edges and said end edges of said topsheet extend outward from said side edges and said end edges of said absorbent core and are joined to said backsheet about said periphery thereby enclosing said absorbent core; and an elastically extensible, longitudinally oriented support strip having laterally oriented ends which is disposed along said longitudinal centerline between said absorbent core and said topsheet, said support strip comprising a laminate of two plies of nonwoven material with an elastic member disposed therebetween, wherein said ends of said support strip are joined to said absorbent core adjacent said end edges of said absorbent structure such that said support strip provides an elastic contractive force which causes at least a portion of said support strip and at least a portion of said topsheet to vertically separate from said absorbent core.

20. The disposable absorbent structure of claim 19 wherein said two plies of nonwoven material comprise a first ply comprising a first nonwoven material and a second ply comprising a second nonwoven material.

21. The disposable absorbent structure of claim 20 wherein said first nonwoven material comprises a carded nonwoven and said second nonwoven material comprises a spunbonded nonwoven.

22. The disposable absorbent structure of claim 19 wherein said elastic member comprises a plurality of elastic strands.

* * * * *

UNITED STATES PATENT AND TRADEMARK OFFICE
CERTIFICATE OF CORRECTION

PATENT NO. : 5,885,268
DATED : March 23, 1999
INVENTOR(S) : Denise Jean Bien et al.

It is certified that error appears in the above-identified patent and that said Letters Patent is hereby corrected as shown below:

Column 6, line 14, "arc" should read -- are --.

Column 8, line 43, "fiber" should read -- fibers --.

Column 12, line 41, "BL30MGA" should read -- BL30MG-A --.

Column 16, line 53, delete "10".

Column 19, line 30, "abiout" should read -- about --.

Column 27, line 28, "alone" should read -- along --.

Signed and Sealed this

Twenty-eighth Day of December, 1999

Attest:

Q. TODD DICKINSON

Attesting Officer

Acting Commissioner of Patents and Trademarks